United States Patent [19]
Powell et al.

[11] Patent Number: 6,060,546
[45] Date of Patent: May 9, 2000

[54] NON-AQUEOUS SILICONE EMULSIONS

[75] Inventors: Virginia V. Powell, East Nassau; Amy-Elizabeth Kasson, Ballston Spa; John A. Kilgour, Clifton Park; An-Li Kuo, Chappaqua, all of N.Y.

[73] Assignee: General Electric Company, Pittsfield, Mass.

[21] Appl. No.: 09/193,347

[22] Filed: Nov. 17, 1998

Related U.S. Application Data

[63] Continuation-in-part of application No. 09/033,788, Mar. 3, 1998, which is a continuation-in-part of application No. 08/708,436, Sep. 5, 1996, Pat. No. 5,760,116.

[51] Int. Cl.$^7$ ..................................................... C08K 5/54
[52] U.S. Cl. ........................ 524/267; 524/268; 524/379; 524/386; 524/389; 524/736; 524/765; 514/772; 424/64; 424/65; 424/78.03; 510/122
[58] Field of Search .................................. 524/379, 386, 524/389, 765, 736, 267, 268

[56] References Cited

U.S. PATENT DOCUMENTS

| | | |
|---|---|---|
| 2,823,218 | 2/1958 | Spier et al. . |
| 3,159,601 | 12/1964 | Ashby . |
| 3,159,662 | 12/1964 | Ashby . |
| 3,220,972 | 11/1965 | Lamoreaux . |
| 3,715,334 | 2/1973 | Karstedt . |
| 3,775,452 | 11/1973 | Karstedt . |
| 3,778,458 | 12/1973 | Morehouse . |
| 3,814,730 | 6/1974 | Karstedt . |
| 4,945,147 | 7/1990 | Policastro et al. . |
| 4,987,169 | 1/1991 | Kuwata et al. . |
| 5,214,118 | 5/1993 | Hawkins et al. . |
| 5,274,065 | 12/1993 | Veith . |
| 5,437,813 | 8/1995 | Akashi et al. . |
| 5,506,289 | 4/1996 | McDermott et al. . |
| 5,529,837 | 6/1996 | Fujiki et al. . |
| 5,571,853 | 11/1996 | Ikeno et al. . |
| 5,674,966 | 10/1997 | McDermott et al. . |
| 5,698,654 | 12/1997 | Nye et al. . |
| 5,717,010 | 2/1998 | Ward et al. . |
| 5,760,116 | 6/1998 | Kilgour et al. . |
| 5,854,336 | 12/1998 | Divone, Sr. et al. . |
| 5,919,437 | 7/1999 | Lee et al. . |

*Primary Examiner*—Melvyn I. Marquis

[57] ABSTRACT

A non-aqueous silicone emulsion containing a silicone phase and an organic phase is useful as a component in various personal care compositions. The silicone phase contains a crosslinked silicone elastomer and a low molecular weight silicone fluid and the organic phase contains an organic liquid.

30 Claims, No Drawings

NON-AQUEOUS SILICONE EMULSIONS

CROSS-REFERENCE TO RELATED APPLICATIONS

The present invention is a Continuation-In-Part application of U.S. application Ser. No. 09/033,788, filed Mar. 3, 1998, which was a Continuation-In-Part application of U.S. application Ser. No. 08/708,436, filed Sep. 5, 1996, U.S. Pat. No. 5,760,116.

FIELD OF THE INVENTION

The present invention relates to non-aqueous emulsions, more specifically to non-aqueous silicone emulsions.

BACKGROUND OF THE INVENTION

Silicones have many uses in a variety of fields. They have found large commercial application in products as diverse as sealants, silicone rubbers, adhesives and cosmetics. Silicone oils have been found to be particularly desirable components of cosmetic compositions because the materials impart a dry, smooth uniform feel to the cosmetic composition among other benefits such as increasing apparent luster (or shine). The general use of silicones in cosmetic formulations has been complicated somewhat by the facts that while lower molecular weight silicones impart desirable properties to a composition they are volatile and have low viscosity, while the silicones that overcome these disadvantages are undesirably viscous.

Thus when it has been desirable to utilize low viscosity silicone oils in a cosmetic application, thickening agents have been employed to increase the solution viscosity and slow down the evaporative loss of the volatile low molecular weight silicone oil. This procedure while effective has the disadvantage of decreasing the spreadability of the silicone oil and leaves a heavy greasy feel on the skin. The spreadability and dry smooth feel are properties associated with low viscosity silicone that imparts a desirable feel or hand to the composition when it is applied as a cosmetic formulation. Materials that have found application in attempting to retain the desirable properties of low molecular weight silicone oils in cosmetic compositions while reducing evaporative losses due to high volatility have been among others fatty acid esters of dextrin, fatty acid esters of sucrose, trimethylsilyl substituted polyvinyl alcohols, trimethylsilyl substituted poly saccharides, cellulose ethers containing fatty acid esters, and organically modified clay minerals. These materials have the disadvantage that the light feeling and spreadability imparted by the low viscosity silicone oil is changed with the result that the composition no longer possesses those properties that suggested the use of the low viscosity silicone oil in the first place. Another disadvantage of these thickening agents or volatility inhibitors is that a large number of them are water soluble and must be used as a water dispersions or solutions. With hydrophobic silicone oils the introduction of water thus necessitates the use of emulsifiers and compatibilizers, complicating the formulation of the cosmetic and generally lowering the stability of the formulation with respect to separation of the component phases.

Recently, another approach to retaining the properties of low viscosity silicone oils in cosmetic compositions has been advanced where the low viscosity silicone oil is combined with the addition polymerization product between an organohydrogen polysiloxane and an alkenyl functionalized organopolysiloxane (U.S. Pat. No. 4,987,169). The organohydrogen polysiloxane utilized in those formulations comprised $HSiO_{1.5}$ ($T^H$), $RSiO_{1.5}$ (T), $RHSiO$ ($D^H$), $R_2SiO$ (D), $R_2HSiO_{0.5}$ ($M^H$) and $R_3SiO_{0.5}$ (M) groups. The crosslinking hydride compound utilized was thus a compound of the general formula: $M_a M^H_b D_c D^H_d T_e T^H_f$. While the cross-linking compound admits T groups either as hydride or substituted by R the preference in this technology is for linear hydride materials because the addition polymerization proceeds more smoothly. The R groups in the above formulas are typical organic substituents known in the art. Subsequently a low molecular weight silicone oil is added to the cross-linked addition polymerized product and the mixture is treated by applying a shearing force. This material may be used by itself as a cosmetic component or as a thickening agent and has the properties of a grease and can be used in a wide variety of industrial lubrication applications as well as the cosmetic application contemplated. The material prepared in this manner can be regarded as a lightly cross-linked elastomer with a volatile, low molecular weight silicone oil dissolved therein. Because the precursor cross-linking hydride is preferably linear and only moderately branched when T groups are incorporated, the addition polymerized product does not possess a tight network of cross-links in the resulting polymer. Linear and lightly crosslinked networks suffer from the disadvantage of having lower efficiency in raising the viscosity of a low molecular weight silicone. In addition to increasing the cost of the product, higher levels of crosslinked silicones result in leaving behind more residue when the volatile, low molecular weight silicone evaporates during use. In some cosmetic applications, e.g. deodorant or antiperspirants, an increased residue is a significant disadvantage as it contributes to staining of the clothing.

Further, linear and lightly crosslinked silicones do not form a film as easily as more tightly crosslinked silicones. The lack of a formation of a film is a disadvantage in a cosmetic application because a film provides a softer, smoother feel as compared to the heavier, less desirable feel of a linear silicone.

For solids, size reduction processes generally result in changing both the average particle size and the particle size distribution. With most solid materials, size reduction techniques usually reduce the average particle size and produce a Gaussian distribution of particle sizes. Consequently, the art dealing with size reduction techniques is primarily concerned with controlling the width of the Gaussian distribution, i.e. how broad or how narrow the particle size distribution is, a property typically measured by the width of the distribution peak at half the peak height of the most prevalent particle size. This is typically referred to as a half-width measurement.

Emulsions can also be subjected to size reduction processes with results similar to those obtained for solid processes. An initial particle size and particle size distribution of an immiscible liquid dispersed in a second liquid phase is converted to one having a smaller average particle size. Typically the particle size distribution of the discontinuous phase in an emulsion is best represented by a Gaussian distribution regardless of whether the particle size distribution is measured before or after size reduction.

While silicones or dispersions of silicones may be emulsified to produce oil-in-water (water is the continuous phase) or water-in-oil (oil is the continuous phase) emulsions, emulsions using other extensive or continuous solvent phases typically present issues of cost and stability. Non-aqueous emulsions of silicones are useful delivery systems for cosmetic applications, particularly when the presence of water initiates a process that changes the nature of the cosmetic composition. While non-aqueous silicone emulsions are known, those utilizing lower molecular weight hydroxylic solvents such as alcohols and glycols typically have sticky or tacky feel and are thus unpleasant when applied to the skin. Further, such materials usually require the application of a high energy process to prepare the non-aqueous emulsion, e.g. homogenization, which only renders the material temporarily stable, i.e. they usually separate after only a few days.

SUMMARY OF THE INVENTION

A non-aqueous silicone emulsion comprises a silicone phase, comprising a silicone elastomer and a low molecular weight silicone compound and an organic phase, comprising an organic liquid.

The non-aqueous silicone emulsion of the present invention exhibits unexpectedly high stability.

DETAILED DESCRIPTION OF THE INVENTION

As used herein, the term "non-aqueous" means the organic phase of the present invention comprises less than 50 parts by weight ("pbw"), more preferably less than 30 pbw, even more preferably less than 10 pbw, and still more preferably less than 1 pbw water per 100 pbw of the organic phase.

Suitable non-aqueous emulsions include both emulsions of a discontinuous organic phase in a continuous silicone phase and emulsions of a discontinuous silicone phase in a continuous organic liquid phase, with the former being the more highly preferred embodiment of the present invention.

In a preferred embodiment, the nonaqueous emulsion of the present invention comprises, based on 100 parts by weight of the emulsion, from 0.1 to 99.9 pbw, more preferably form 5 to 95 and even more preferably from 20 to 80 pbw of the silicone phase, and from 0.1 to 99.9 pbw, more preferably more preferably form 5 to 95 and even more preferably from 20 to 80 pbw of the organic phase.

In a preferred embodiment, the silicone phase comprises from 0.005 to 30 pbw, more preferably from 0.01 to 20 pbw, even more preferably from 0.5 to 15 pbw of the silicone elastomer and from 70 to 99.995 pbw, more preferably from 80 to 99.99 pbw, even more preferably from 85 to 99.95 pbw of the low molecular weight silicone compound.

In a preferred embodiment, the non-aqueous silicone emulsion of the present invention comprises a silicone and a non-aqueous organic hydroxylic solvent, wherein said non-aqueous emulsion comprises a continuous non-aqueous phase.

1. Silicone Phase
   i Silicone Elastomer

In a preferred embodiment, the silicone elastomer forms a crosslinked three dimensional network that does not dissolve in, but is capable of being swollen by the low molecular weight silicone. The crosslinking may be provided by molecular entanglements, for example, entanglement of highly branched silicone polymers or, more preferably, by covalent bonding. While not wishing to be bound by theory, it appears that the swollen silicone elastomer network serves to stabilize the emulsion of the present invention.

The amount of crosslinking present in the crosslinked silicone elastomer network may be characterized with respect to the degree of swelling exhibited by the network in the low molecular weight silicone fluid. In a preferred embodiment, the crosslinked structure of the silicone elastomer is effective to allow the network to be swollen by the low molecular weight silicone fluid from its original volume to a swollen volume that is a factor of from 1.01 to 5000, more preferably from 2 to 1000, and even more preferably from 5 to 500, times its original volume.

The silicone elastomer contains "D" structural units, and may optionally include "T" structural units, or "Q" structural units, or both T and Q structural units. The T and Q structural units provide branching sites and potential crosslinking sites. Branching and crosslinking sites may also be provided by the R substituent groups bonded to silicon atoms of each of two or more of the siloxane chains of the silicone elastomer.

In addition to the selection of reactive substituent groups to provide possible crosslinking sites, substituent groups which are non-reactive under anticipated processing and use conditions may be selected to modify the properties of the silicone elastomer by, for example, providing surfactant groups to promote formation of an emulsion with the organic solvent, or enhancing the compatibility of the elastomer with organic additives, such as, for example, fragrances, or modifying the aesthetic or sensory characteristics, for example, tactile properties or "feel", of the silicone phase of the present invention. Suitable substituent groups include, for example, H, hydroxyl, monovalent acyclic hydrocarbon radicals, monovalent alicyclic hydrocarbon radicals, monovalent aromatic hydrocarbon radicals, ester radicals, thioester radicals, amide radicals, polyester radicals, polythioester radicals, polyamide radicals ether radicals, polyether radicals.

As used herein, the terminology "acyclic hydrocarbon radical" means a straight chain or branched hydrocarbon radical, preferably containing from 2 to 50 carbon atoms per radical, which may be saturated or unsaturated and which may be optionally substituted or interrupted with one or more functional groups, such as, amino, carboxyl, cyano, hydroxy, halo, mercapto, mercaptocarbonyl, dihydroxyphosphinyl, oxo, oxy, alkoxy, aryl, aryloxy. Suitable monovalent acyclic hydrocarbon radicals include, for example, methyl, sec-butyl, tert-butyl, hexyl, cetyl, isostearyl, propenyl, butynyl, methoxy, hydroxypropyl, aminoethyl, cyanopropyl, carboxyethyl, chloropropyl, acrylo, methacrylo.

As used herein, the terminology "alicyclic hydrocarbon radical" means a radical containing one or more saturated hydrocarbon rings, preferably containing from 4 to 10 carbon atoms per ring, per radical which may optionally be substituted on one or more of the rings with one or more alkyl or alkylene groups, each preferably containing from 2 to 6 carbon atoms per group, or other functional groups and which, in the case of two or more rings, may be fused rings. Suitable monovalent alicyclic hydrocarbon radicals include, for example, cyclohexyl, cyclooctyl.

As used herein, the term "aromatic hydrocarbon radical" means a hydrocarbon radical containing one or more aromatic rings per radical, which may optionally be substituted on the one or more aromatic rings with one or more alkyl or alkylene groups, each preferably containing from 2 to 6 carbon atoms per group, or other functional groups and which, in the case of two or more rings, may be fused rings. Suitable monovalent aromatic hydrocarbon radicals include, for example, phenyl, styryl, α-methylstyryl, naphthyl.

Suitable ester radicals include alkylcarbonyloxyalkylene radicals, such as, for example, methycarbonyloxypropylene.

Suitable thioester radicals include alkylthiocarbonylalkylene radicals, such as, for example, methythiocarbonylpropylene.

Suitable amide radical include alkylamidoalkylene radicals, such as for example, methylamidopropylene.

Suitable polyester radicals include, for example, those according to the structural formula:

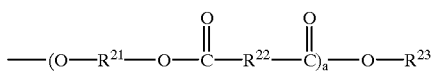

wherein:
$R^{21}$ represents the residue of the diol or diol equivalent ("diol residue"),
$R_{22}$ represents the residue of the diacid or diacid equivalent (diacid residue"),
a is an integer from 1 to 20;
$R^{23}$ is H, alkyl, hydroxalkyl, and each $R^{21}$ and $R^{22}$ is independently a divalent acyclic hydrocarbon radical, such as, for example, dimethylene, trimethylene, tetramethylene, hexamethylene and octamethylene, a divalent alicyclic hydrocarbon radical, such as, for example, 2,2,4,4-tetramethyl-1,3-cyclobutylene, 1,4-cyclohexylene, cyclohexylene-1,4-dimethylene, 1,4-cyclooctylene, or a divalent aromatic hydrocarbon radical, such as, for example, 1,2-phenylene, 1,3-phenylene, 1,4-phenylene, 2,6-naphthalene, 2,7-phenathrylene, such as, for example, those polyester substituent groups disclosed in U.S. Pat. Nos. 5,214,118, 3,778,458 and 4,945,147.

Suitable polythioester radicals and polyamide radicals include analogs of the above described polyester radicals, wherein the divalent oxygen atoms of the polyester radical is replaced by sulfur or nitrogen, such as, for example, the polyamide radicals disclosed in U.S. Pat. Nos. 5,274,065, and 5,437,813.

As used herein the term "polyether radical" means a monovalent group according to the structural formula:

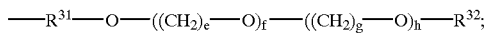

wherein $R^{31}$ is alkylene,
$R^{32}$ is H, alkyl, alkenyl, alkoxy, carboxy, hydroxyalkyl;
e and g are each independently integers of from 1 to 12; and
g and h are each independently integers of from 0 to 100; and
$1 \leq g+h \leq 200$.

Suitable silicone elastomers can be made by known synthetic techniques, such as, for example, addition polymerization, condensation polymerization, free radical polymerization.

In a preferred embodiment, the silicone elastomer is made by an addition polymerization reaction, more preferably, a hydrosilylation reaction.

In a highly preferred embodiment, the silicone elastomer is made by a hydrosilylation reaction between an alkenyl silicone precursor and a hydrogen silicone precursor. Generally, the alkenyl silicone precursor compound will be an organosiloxane or organopolysiloxane having two or more alkenyl groups per molecule on average and the hydrogen silicone precursor will be an organohydrogensiloxane having two or more silicon hydride groups per molecule on average. Such compounds are described in a multiplicity of U.S. patents particularly U.S. Pat. Nos. 5,506,289; 5,674,966; 5,717,010; 5,571,853; and 5,529,837 herewith specifically incorporated by reference. The alkenyl functionality and the hydride functionality may be combined into one molecule self-curing molecule or compound as is taught in U.S. Pat. No. 5,698,654. In many embodiments the silicone elastomer comprises particles which may or may not be finely divided, of elastomer dispersed in a carrier oil, preferably a silicone oil.

In a very highly preferred embodiment, the non-aqueous emulsion of the present invention comprises:
the hydrosilylation addition product of
(1) a linear alkenyl stopped polyorganosiloxane having the formula:

where the subscript x is a number greater than 500 preferably greater than 600, more preferably greater than 700, and most preferably greater than 800, the subscript y is a number ranging from zero to about 20, preferably ranging from zero to about 10, more preferably ranging from zero to about 5, and most preferably ranging from zero to about 4, the subscript a is a number ranging from 0 to 2, subject to the limitation that a+y is within the range of from 1 to about 20, preferably from one to about 10, more preferably from about 1.5 to about 10, and most preferably from about 1.5 to about 6, with $M^{vi}$ defined as:

$$R^1R^2R^3SiO_{1/2}$$

where $R^1$ is a monovalent unsaturated hydrocarbon radical having from two to ten carbon atoms, preferably styryl, allyl and vinyl, more preferably allyl and vinyl and most preferably vinyl and $R^2$ and $R^3$ are each independently selected from the group of from one to fifty, carbon atom monovalent hydrocarbon radicals, more preferably from one to forty, carbon atom monovalent hydrocarbon radicals, even more preferably one to twenty carbon monovalent hydrocarbon radicals, still more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl with D defined as:

$$R^4R^5SiO_{2/2}$$

where $R^4$ and $R^5$ are each independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl;
with $D^{vi}$ defined as:
$D^{vi}=R^6R^7SiO_{2/2}$ where $R^6$ is a monovalent unsaturated hydrocarbon radical having from two to ten carbon atoms, preferably styryl, allyl and vinyl, more preferably allyl and vinyl and most preferably vinyl and $R^7$ is independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-buty, tert-buty, pentyl, hexyl, heptyl, phenyl, benzyl, and mesityl; and most preferably from the group consisting of methyl and phenyl and with M defined as $M=R^8R^9R^{10}SiO_{1/2}$ with $R^8$, $R^9$, and $R^{10}$ each independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl and (2) a resin having the formula:

$$(M^H{}_w Q_z)_j$$

where Q has the formula $SiO_{4/2}$ and where $M^H$ has the formula $H_b R^{11}{}_{3-b} SiO_{1/2}$ with the subscript b ranging from 1 to 3, where $R^{11}$ is a one to forty carbon atom monovalent hydrocarbon radical, preferably a one to twenty carbon monovalent hydrocarbon radical, more preferably selected from the group consisting of methyl, ethyl, propyl, iso-propyl, n-butyl, iso-butyl, sec-butyl, tert-buty, pentyl, hexyl, heptyl, phenyl, benzyl, and mesityl; and most preferably selected from the group consisting of methyl and phenyl with the subscripts w and z having a ratio of 0.5 to 4.0 respectively, preferably 0.6 to 3.5, more preferably 0.75 to 3.0, and most preferably 1.0 to 3.0; and the subscript j ranging from about 2.0 to about 100, preferably from about 2.0 to about 30, more preferably from about 2.0 to about 10, and most preferably from about 3.0 to about 5.0; and (3) a low molecular weight silicone, wherein the mixture of low molecular weight silicone with the reaction product of (1) and (2) has been subjected to shearing forces that affect the average particle distribution and the distribution has certain unique properties;

wherein the addition product of the linear alkenyl stopped polyorganosiloxane (1) and resin (2) dispersed in the low molecular weight silicone is emulsifiable with the organic liquid.

In a preferred embodiment, the hydrosilylation reaction is carried out in at least a portion of the low molecular weight silicone and in the presence of a hydrosilylation catalyst selected from the group of ruthenium, osmium, rhodium, iridium, palladium and platinum hydrosilylation catalysts. Exemplary of such catalysts are those described in U.S. Pat. Nos. 2,823,218; 3,159,601; 3,159,662; and 3,775,452.

ii. Low molecular weight silicone fluid

The low molecular weight silicone fluid is an organosilicon compound having a viscosity of below about 1,000 centistokes, preferably below about 500 centistokes, more preferably below about 250 centistokes, and most preferably below 100 centistokes, at 25° C. Thus low molecular weight cyclic silicones such as $D_3$, $D_4$, $D_5$, and $D_6$ (i.e. $D_f$ where the subscript f ranges from 3 to 6) where D is as previously defined with $R^4$ and $R^5$ preferably methyl as well as low molecular weight linear silicones having the formula $$M'D'_i M'$$

where the substituents on D' are independently selected from the same substituents as previously defined for D and M' has the formula $$R^{12} R^{13} R^{14} SiO_{1/2}$$

where $R^{12}$, $R^{13}$ and $R^{14}$ are each independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, styryl, α-methyl styryl, benzyl, and mesityl; and most preferably from the group consisting of methyl and phenyl; and the subscript i ranges from 0 to about 300, preferably from 0 to about 100, more preferably from 0 to about 50, and most preferably from 0 to about 20 are such volatile, silicones. Preferably component (3) is a low molecular weight silicone.

iii. Preferred method for making silicone phase

The materials used to prepare the gels of the present invention have been defined in terms of formulas that recite structural elements M, D, T and Q within the definitions commonly accepted in the practice of silicone chemistry. As individual molecules, or as pure compounds, the subscripts of these formulas can assume only integral values (including zero where appropriate). As complex mixtures of compounds, each of which individually satisfies the molecular definition, the subscripts in describing the mixture will assume non-integral values (including zero where appropriate). However, those non-integral values for a given subscript will still range between the upper limit and the lower limits of the range for that particular subscript when integral values are stipulated. Thus, for example in the pure compound description of component (1), the subscript a may have the values 0, 1 or 2. As a mixture of compounds, component (1) will have an average value for the subscript a that is dependent on the number of individual molecular species having a value for the subscript a that is equal to 0, 1, and 2. The same explanation holds for components (2) and (3).

Thus, the average subscripts for component (1), when component (1) is a vinyl functionalized silicone as the specific alkenyl functionalization and is a mixture of various vinyl containing compounds, as defined, will span a range of vinyl equivalent weights ranging from about 1,500 to about 150,000, preferably from about 4,500 to about 110,000, more preferably from about 10,000 to about 70,000, and most preferably from about 15,000 to about 45,000. It is to be noted that these equivalent weights are specific equivalent weights for vinyl substitution, substitution with other olefinic substituents would generate a different but comparable range of equivalent weights. Likewise, the average subscripts for component (2) as a mixture, as defined, will span a range of hydride equivalent weights ranging from about 80 to about 190, preferably from about 82 to about 170, more preferably from about 85 to about 150, and most preferably from about 87 to about 130.

Further it is desirable that the alkenyl functionality present in component (1) ranges on average of from about 2 to about 20 alkenyl groups per molecule, preferably from about 1 to about 10 alkenyl groups per molecule, more preferably from about 1.5 to about 10 alkenyl groups per molecule, and most preferably from about 1.5 to about 6 alkenyl groups per molecule. Additionally, it is desirable that the hydride functionality present in component (2) ranges on average of from about 2 to 400 SiH groups per molecule, preferably from about 8 to about 100 SiH groups per molecule, more preferably from about 8 to about 50 SiH groups per molecule, and most preferably from about 8 to about 20 SiH groups per molecule.

Components (1) and (2) (as pure compounds or mixtures) are catalytically reacted together in the presence of component (3) to produce a gel having a polymer content that is approximately from about 5 to about 75 weight percent crosslinked polymer, preferably from about 10 to about 60 weight percent crosslinked polymer, more preferably about 15 to about 40 weight percent crosslinked polymer, and most preferably about 20 to about 35 weight percent crosslinked polymer with the balance being the volatile, low molecular weight silicone oil. Once this initially produced gel is prepared, it is mixed with an additional quantity of a volatile, low molecular weight silicone, i.e. additional component (3)

which is possibly different from the component (3) used to prepare the initially produced gel, and subjected to mixing or shearing forces to produce a uniform liquid gel that is from about 1 to about 25 weight percent crosslinked polymer, preferably from about 2 to about 20 weight percent crosslinked polymer, more preferably from about 3 to about 15 weight percent crosslinked polymer, and most preferably from about 3 to about 10 weight percent crosslinked polymer with the balance being the volatile, low molecular weight silicone oils, component (3) or a mixture of compounds satisfying the definition of component (3).

The gel initially produced is sufficiently viscous that liquid flow is not ordinarily observable. As a crosslinked polymeric material, the gel initially produced, having 25 weight percent crosslinked polymer network, has a Durometer hardness number, ASTM D-2240-91, of at least 5, preferably of at least 7, more preferably of at least 10 and most preferably of at least 15. ASTM test numbers for the Durometer hardness test are indicative of a material sufficiently resistant to flow that it may fairly be characterized as a solid.

In recent years, the personal care industry has found that the use of a variety of silicone polymers ranging from very low to very high molecular weight can provide improved product flow and a smooth, non-greasy feel in a wide range of applications. So for example, silicone polymers have been used in formulations for antiperspirant/deodorants, skin lotions, creams, hair care, cosmetics and the like. While these silicone polymers provide the desired performance characteristics to personal care products, they have traditionally required a delivery system that includes non-silicone thickening agents. These non-silicone thickening agents are generally undesirable as they have a negative impact on the desired silicone feel.

Recent technology that teaches the use of crosslinked silicone polymers for thickening agents fails to recognize the need to generate the unique and desirable distribution of crosslinked silicone polymer particles that create superior performance characteristics including the smooth silky feel and high viscosity for optimal thickening effects. This technology does not adequately define a process for generating the most highly desired distribution of these particles. In addition, some of the processing methods suggested by this technology are limited to only a small range of crosslinked silicone polymer that can be useful in the instant invention. Thus as the nature of the crosslinked silicone polymer changes to provide for the desirable, more efficient use of polymer material, the suggested shearing methods using low levels of compression (colloid mills and the like), mechanical cutting shear (rotor/stator mills) or fracture (hammer mills) fail to provide the desired crosslinked silicone polymer particles of the required size and distribution. Further, they fail to define a method for processing the crosslinked silicone polymer in an economical manner.

Surprisingly a process has been discovered for providing a thickener for carrier silicone oil comprising the use of silicone particles having a unique distribution of particle sizes. Further, it has been discovered that the use of high flow induced shear and particle elongation in addition to providing an economical method for processing crosslinked silicone polymers, also generates a unique and highly desirable particle size distribution that provides the desired smooth, silky feel while maintaining high viscosity and thickening properties. Further this method of processing is applicable to the entire range of desirable crosslinked silicone polymers.

While some of the physical properties of the thickening agent are determined by the chemical structure of the crosslinked silicone polymer, the particle size and distribution are key to the highly desirable thickening (viscosity) and feel properties of the product. The efficient thickening behavior is the result of having large particle sizes present to increase the fluid viscosity. The size of the large particles is limited by the need to avoid particle so large that they form visible balls of gel during application. The superior feel is the result of generating smaller particles that improve lubricity during spreading on the skin. If the crosslinked silicone polymer is degraded to too small particles or to homogeneous fluids, they become undesirably heavy or greasy in feel. Thus preparing an efficient thickening agent with the superior feel requires the ability to generate a wide distribution of particles.

Surprisingly, the use of flow induced shear and particle elongation particularly at high stress levels provides a unique distribution of particle sizes when used to process crosslinked silicone polymers. Where as the normal expectation is to find a monomodal or possibly bimodal distribution of particle sizes when employing stress to break down particles, it is found that particularly high flow induced shear and particle elongation produce multiple distributions of particle sizes.

Earlier experiments have shown that the particles prepared in this invention are not fully swollen in material as dilute as five percent elastomer content and 95% cyclic siloxanes. However, if the elastomer is further diluted below elastomer contents of about three percent, the particle swells to its full extent. Thus the particle sizes reported in this invention demonstrate fully extended particles, while those used in most applications are of proportionally smaller actual volume depending on the available solvent. Since for a given particle composition it is possible to measure how much additional solvent may be absorbed, it is possible to back calculate the particle size for any given concentration once the full extended particle size is known. Further, it is within the scope of this invention to prepare smaller particles at a higher elastomer concentration and then swell them at a later time with additional solvent to achieve a larger particle size.

For the product of this invention, the particle size distribution comprises a multiple series of individual and often overlapping particle size populations. Taken together they provide a broad distribution of both large and small particles that impart both high efficiency and viscosity as well as a good feel and lubricity. The individual particle size populations generally fit a log normal particle size distribution and as measured at full range from an average of about 10 microns to an average of about 600 microns. When for a specific application the particles are not fully swollen, the population of particle sizes, i.e. the particle size distribution, will cover proportionally smaller sizes and with a shift to ranges over lower particle sizes. The particle size distribution comprises a series of multiple, identifiable particle populations ranging from less than about 1 microns on swelling to about 600 microns after swelling. It is preferable for the average particle size range when measured in a fully swollen state to cover from about 1 to about 500 microns, more preferably to include about 1 to about 400 microns and most preferably to include about 1 to about 300 microns after solvent swelling.

The compositions of the present invention are characterized by being dispersions of an organic polymeric elastomer, preferably a silicone elastomer, in a suitable solvent and having a particle size distribution characterized by the presence of three local maxima in the particle size distribution: 1) a local maximum ranging from about 21 to about 26 microns, 2) a local maximum ranging from about 33 to about 38 microns, and 3) a local maximum ranging from about 50 to 60 microns. As local maxima, these three local maxima appear as identifiable spikes in a plot of population versus particle diameter. It is to be emphasized that the compositions of the present invention may possess more than these three local maxima in a plot of population versus particle size, but the compositions of the present invention always possess these three local maxima. Depending on other features of the particle size distribution, the subjective properties of the composition vary from a so-called stiff creamy feel when the distribution is skewed to higher particle diameters to a light creamy feel when the distribution is centered around these three local maxima to a heavy greasy feel when the distribution is skewed to lower particle diameters. These numbers are specific to the instrumental method of analyzing the particle size distribution, specifically using a Malvern Mastersizer fitted with a 300 mm lens.

The process for making suitable crosslinked silicone polymer particles for use in the current application involves the preparation of a crosslinked silicone polymer, often in a low molecular weight silicone fluid. The material may then be further swollen with additional solvent either the same or different than that used in making the crosslinked silicone polymer. The crosslinked silicone polymer is then subjected to force to break it into small particles often in the presence of additional silicone fluid. It is a discovery of this invention that the superior method of breaking the polymer into small particles is through high flow induced shear. In this method, the slurry is first diluted, including the crosslinked silicone polymer and any additionally desired solvent, and then forced through an orifice under pressure generating flow induced shear and particle elongation. In this method, the flow induced shear and particle elongation occur both as the material passes through the orifice and in the entry region to the orifice. Although some material may be cleaved by hitting the edge of the orifice, it is this flow induced shear and particle elongation that ultimately tears the crosslinked silicone polymer apart and creates small particles.

The magnitude and profile of the flow induced shear in this process is controlled by several parameters including the pressure, orifice geometry and fluid viscosity which in part reflects the temperature, flow and shear characteristics of the fluid. Pressure may be defined as the pressure drop across the orifice. Increasing pressure drop increases the flow induced shear such that the crosslinked silicone polymer is more rapidly torn into the desired particle sizes and with a wider, more desirable distribution of particle sizes. Generally, high flow induced shear is associated with higher pressure drops for a particular orifice geometry and fluid viscosity.

The orifice geometry at a given pressure drop also determines the nature of high flow induced shear. Orifice geometry is a very flexible characteristic with a variety of shapes and sizes. Thus for example, an orifice might have an opening shape that is round, ovoid, rectangular or annular. Such orifices may be completely open or contain a pin or other obstruction at the opening. There may be one opening or many of the same or different geometries. In general as the orifice gets larger at the same pressure and fluid viscosity, the distribution of particle sizes becomes wider and more desirable. Similarly the length of the path traveled by the fluid may be long or short, straight or bent. In general as the length of the orifice becomes shorter, the flow induced shear increases and smaller more widely distributed particles are generated. The orifice size also influences flow induce shear in the entry region to the orifice. Thus as the ratio increases such that the material flows from a larger tube to a smaller orifice the particle size distribution is increased.

Fluid viscosity also determines the flow induced shear. As the viscosity of the fluid increases, the flow induced shear increases with the attendant desirable results. Viscosity will be influenced by the temperature, a lower more constant temperature giving higher viscosity is desirable. Similarly, materials exhibiting shear thinning, as some silicones are known to do, will have a lower flow induced shear in the orifice, thus increasing the particle size and narrowing the distribution. While the viscosity of the initial slurry of elastomer fed to the process may be difficult to measure, after processing the viscosity can be measured and for the first several passes through the process the viscosity of the elastomer dispersion increases. Because the material being processed is a dispersion or suspension of elastomer particles in a solvent, viscosity may be affected by a consideration of the so-called solids level. As the solids level is increased, i.e. the amount of solvent present being progressively reduced, resistance to flow increases, which can sometimes be measured as an increase in viscosity.

Taken together, these parameters are the major factors in determining flow induced shear. Depending upon a particular environment, any one or more of these three may be the dominant, i.e. most critical factor(s), in deciding the actual flow induced shear. High dynamic shear is that which is sufficient to break down the crosslinked particles to the desired size and distribution. In some instances this is accomplished in a single pass through the orifice, or alternatively a few to several passes may be required to achieve the desired particle size. In general fewer passes and wider particle size distribution are the more desired economic and performance results coming from high flow induced shear.

Flow induced particle elongation occurs as the crosslinked silicone polymer converges under pressure as it is forced to flow toward the orifice, flowing from a large diameter environment to the small diameter opening. As the particle travels through this region, it is elongated and smaller particles generated. The critical factors include pressure, fluid viscosity and the ratio of the cross sectional areas of the feed chamber to orifice. As the pressure is increased the particle elongation is increased and more efficient particle size breakage is achieved. Similarly, as the viscosity of the fluid is increased, the particle elongation is increased. As the ratio of the cross sectional areas of the feed chamber to the orifice is increased, the particle elongation is increased. In general as the particle elongation increases the efficiency in breaking down particles increases requiring fewer passes.

The pressure range desirable for sufficient flow induced shear and particle elongation is above 500 psi. Preferably it is above 1000 psi, more preferably over 1500 psi and most preferably over 2000 psi. The viscosity should be above 500 ctks. Preferably is should be over 750 ctks more preferably over 1000 ctks and most preferably over 5000 ctks. The orifice size is limited by the ability of the pumping system to maintain sufficient pressure. As a practical matter it is desirable to have an orifice size of less than 0.5 square inches, preferably less than 0.1 square inches, more preferably less than 0.05 sq. in, and most preferably less than 0.01 sq. inch.

The interaction of all of these operating variables combine to produce a process where the elastomer dispersion is reduced in average particle size and the unique particle size distribution is produced. Generally unless the elastomer dispersion is processed at a very high pressure drop, conversion to a desirable composition is not achieved in a single pass. There is thus a correlation between the applied pressure drop and the number of passes through the processing equipment that the elastomer dispersion must be subjected to in order to convert the material to the desired composition. This is reflected by the following dimensionless correlation equation that determines the number of passes, $N_p$ necessary to produce acceptable material for a given pressure drop, $P_d$:

$$N_p = 82{,}799 P_d^{(-1.1696)}$$

To some extent this equation is arbitrary and varies as the definition of what constitutes acceptable material. Material possessing a particle size distribution characterized by three peaks or three local maxima in the particle size distribution: 1) a local maximum ranging from about 21 to about 26 microns, 2) a local maximum ranging from about 33 to about 38 microns, and 3) a local maximum ranging from about 50 to 60 microns constitutes material that is acceptable.

Further, it is possible to generate a dimensionless correlation which correlates the resulting average particle size (as determined by a Malvern Mastersizer™), $S_p(\text{avg.})$, with the pressure drop, $P_d$, orifice cross-sectional area, $O_a$, and the number of passes, $N_p$.

$$S_p(\text{avg.}) = K + C_1 P_d + C_2 O_a + C_3 N_p,$$

where K is an intercept, and the various $C_i$'s are coefficients associated with the indicated variable, i.e. $C_1$ is the pressure drop coefficient, $C_2$ is the orifice cross-sectional area coefficient, and $C_3$ is the number of passes coefficient. The various operating ranges are defined in the following tables:

TABLE A

Operating Ranges

| Parameter | Minimum (from about) | Maximum (to about) |
|---|---|---|
| $P_d$ | 500 | 35000 |
| $O_a$ | 0.5 | 0.0001 |
| $N_p$ | 1 | 100 |
| $S_p(\text{avg.})$ | 585 | 16 |
| K | 639 | 639 |
| $C_1$ | −0.026 | 0.026 |
| $C_2$ | −61 | −61 |
| $C_3$ | 2.87 | 2.87 |

TABLE B

Preferred Operating Ranges

| Parameter | Minimum (from about) | Maximum (to about) |
|---|---|---|
| $P_d$ | 1000 | 30000 |
| $O_a$ | 0.1 | 0.002 |
| $N_p$ | 1 | 50 |
| $S_p(\text{avg.})$ | 3 | 610 |
| K | 639 | 639 |
| $C_1$ | −0.026 | −0.026 |
| $C_2$ | −61 | −61 |
| $C_3$ | 2.87 | 2.87 |

TABLE C

More Preferred Operating Ranges

| Parameter | Minimum (from about) | Maximum (to about) |
|---|---|---|
| $P_d$ | 1500 | 27500 |
| $O_a$ | 0.005 | 0.0003 |
| $N_p$ | 1 | 30 |
| $S_p(\text{avg.})$ | 10 | 603 |
| K | 639 | 639 |
| $C_1$ | −0.026 | −0.026 |
| $C_2$ | −61 | −61 |
| $C_3$ | 2.87 | 2.87 |

TABLE D

Most Preferred Operating Ranges

| Parameter | Minimum (from about) | Maximum (to about) |
|---|---|---|
| $P_d$ | 2000 | 25000 |
| $O_a$ | 0.01 | 0.0005 |
| $N_p$ | 1 | 10 |
| $S_p(\text{avg.})$ | 18 | 589 |
| K | 639 | 639 |
| $C_1$ | −0.026 | −0.026 |
| $C_2$ | −61 | −61 |
| $C_3$ | 2.87 | 2.87 |

Because the number of passes, $N_p$, correlates with the pressure drop, $P_d$, the equation for the number of passes may be substituted into the average particle size equation. This mathematical substitution underscores the strong pressure drop dependence of the process. Simply stated, the process of the present invention (to yield the composition of the present invention) is a process where an elastomer dispersion is subjected to a pressure and passed through an orifice at a specified pressure drop wherein the average particle size is reduced and the particle size distribution yields certain specified local maxima. Any process that achieves this conversion by means of a pressure drop and an orifice is a process of the present invention. Applicants note that the pressure drop as used herein has the dimensions of pounds per square inch (psi.), the orifice cross-sectional area has the dimensions of square inches (sq. in. or in.²), and particle sizes or average particle size has the dimension of microns. As the orifice size decreases the pressure must be increased to maintain throughput. For this reason, a smaller orifice size is listed under the column heading "maximum" in describing the ranges, because smaller orifice size and increased pressure create the same global effect.

Finally, it should be emphasized that the intercept and coefficients in the process variable equation may change depending on the specific machine used. The data presented herein represent the results of a correlation on a few selected machines are thus illustrative rather than constituting a definition or limitation. Thus while the process variables are fairly precisely defined, the intercept, K, and the coefficients $C_1$, $C_2$, and $C_3$ are more likely to depart from the values reported herein than would the actual process variables. Irrespective of the actual machine and the actual values of the intercept and these coefficients in a process variable correlation, any process accomplishing the conversion of particle size to that defined herein is intended to be covered by the appended claims.

The generation of the desired particle size is in part determined by the swelling of the particles before application of the flow induced shear and particle elongation. As the particle swells with solvent, internal stress is developed which lowers the level of shear and particle elongation required to tear apart the particle. Thus more swelling or lower crosslinked silicone polymer concentration in the slurry being processed increases the internal stress and makes the process more efficient. It is desirable to dilute to a crosslinked polymer concentration of less than 60% by weight solids. It is preferable to swell and dilute the crosslinked silicone polymer to less than 50% by weight solids, more preferable to swell the crosslinked polymer to less than 40% by weight solids and most preferable to dilute the crosslinked polymer to less than 30% by weight solids content.

The resistance to flow of the initially produced gel is overcome by high speed mixing or shearing wherein the resulting composition or mixture is a uniform liquid and has a viscosity ranging from about 500 to about 150,000 centistokes at 25° C., more preferably the resulting viscosity of the composition or mixture is from about 1,000 to about 100,000 centistokes at 25° C., and most preferably the resulting viscosity of the composition or mixture is from about 10,000 to about 60,000 centistokes at 25° C. By shearing, Applicants mean the imposition of a force upon the composition where the mixture is treated using a two roll mill, a colloid mill, a Gaulin homogenizer, a Sonolator, Ross™ mixer, Aviston™ mixer, Microfluidizer, etc. The elastomer dispersions processed by the process of the present invention are comprised of an elastomer gel and a low molecular weight silicone. The process of the present invention used to achieve the composition of the present invention may be applied to an elastomer dispersion or a dispersion of a gel or a gel. Subjecting these compositions to a shearing force produces a component suitable for use in personal care or cosmetic applications that has an improved spreadability and an improved substance or feel because of the presence of the composition of the present invention possessing a unique particle size distribution.

The silicone phase may optionally include a minor amount of organic components that are miscible with the silicone phase and immisible or partially miscible with the organic phase, such as, for example, fragrances or oils.

The Organic liquid

The organic liquid may be any organic compound that is in the liquid state at room temperature, for example, about 25° C., and about one atmosphere pressure, that is substantially inert to the silicone phase, that is, does not undergo a chemical reaction with any of the components of the silicone phase, under the anticipated conditions of processing and use and that is suitable for use in the intended end-use application, such as, for example, a cosmetic composition, to be prepared from the non-aqueous emulsion of the present invention.

In a preferred embodiment, the organic liquid is a polar liquid that exhibits a dipole moment of from 0.9 to 4.5.

In a highly preferred embodiment, the organic liquid is a organic hydroxylic liquid, containing for example, one or more of alcohols, glycols, polyhydric alcohols and polymeric glycols. More preferably, the organic liquid is selected from of alcohols including polyhydric alcohols, glycols, including polymeric glycols, and mixtures thereof. Preferably, the polar organic liquid contains an ($C_1$–$C_{12}$) alcohol, such as for example, ethanol, propyl alcohol and iso-propyl alcohol, a ($C_2$–$C_{12}$)glycol, such as for example, propylene glycol, dipropylene glycol, tripropylene glycol, butylene glycol, iso-butylene glycol, 2- and methyl-3-propane diol, a polyhydric alcohol, such as for example, glycerin erythritol and sorbitol, or a polymeric glycol, such as for example, polyethylene glycol, polypropylene glycol mono alkyl ethers and polyoxyalkylene copolymers. In a highly preferred embodiment, the organic liquid is selected from ethanol, propyl alcohol, iso-propyl alcohol, propylene glycol, dipropylene glycol, tripropylene glycol, butylene glycol, iso-butylene glycol, 2-methyl-3-propane diol, glycerin, erythritol sorbitol, polyethylene glycol, polypropylene glycol mono alkyl ethers, polyoxyalkylene copolymers.

Emulsifying agent

In a preferred embodiment, the emulsion of the present invention comprises one or more emulsifying agents. Suitable emulsifying agents useful in preparing the emulsions of the present include, for example, silicone-containing emulsifying agents, emulsifying agents derived from sorbitan compounds and emulsifying agents derived from fatty alcohols and polymeric emulsifiers, more preferably the emulsifying agent is selected from the group consisting of fatty acid esters, sorbitan sesquioleate, sorbitan oleate, sorbitan isostearate, polyglyceryl-3 oleate, alkoxylated alcohols such as laureth-4, laureth-7, deceth- 12, steareth-10, hydroxylated or alkoxylated derivatives of silicone compounds such as dimethicone copolyol, cetyl dimethicone copolyol, and lauryl methicone copolyol, glyceryl esters such as polyglyceryl4-isostearyl polymeric emulsifiers, such as alkylpolyglucosides and mixtures thereof; and most preferably the emulsifying agent is dimethicone coployol which may or may not be dispersed in a silicone oil or cyclomethicone diluent. In a preferred embodiment, the dimethicone copolyol emulsifier has limited solubility in the silicone phase to be emulsified.

Making the non-aqueous emulsion

The silicone phase and the organic liquid are mixed to form the non-aqueous emulsion of the present invention. In a preferred embodiment, the organic liquid is slowly added to the silicone phase while subjecting the combined organic liquid and silicone phase to low shear mixing, such as, for example, in a mixing tank equipped with a propeller-type stirrer, and then the mixture so formed is homogenized, for example, in a Sonolator apparatus, a Gaullen homogenizer or a high shear mixer, such as an Eppenbach Mixer, to form the emulsion. In a more highly preferred embodiment, an emulsifying agent is combined with the silicone phase prior to adding the organic liquid to the silicone phase.

3. Personal care compositions

The personal care applications where the emulsions of the present invention may be employed include, but are not limited to, deodorants, antiperspirants, skin care products, hair care products such as shampoos, mousses, styling gels, protective creams, such as sunscreen, and color cosmetics such as lip products or lipsticks, foundations, blushes, makeup, and mascara; and other cosmetic formulations where silicone components have been added.

Suitable personal care compositions are made by combining one or more of the above components with the emulsion of the present invention. The components may be added before or after formation of the non-aqueous emulsion In a preferred embodiment, any such desired components are added to the silicone phase or to the organic liquid prior to mixing the silicone phase with the organic liquid to form the non-aqueous emulsion. Similarly, the compositions of the present invention also have utility as drug delivery systems for topical application of medicinal compositions that are to be applied to the skin.

In a preferred embodiment, a personal care composition comprises non-aqueous emulsion of the present invention and one or more water-sensitive dermatological active agents or cosmetic active agents, such as for example, ascorbic acid or an enzyme, particularly a protease, such as for example, enzyme sold under the trade name SUBTILISIN SP 544 by Novo Nordisk or the enzyme sold under the trade name LYSOVEG by Laboratoires Serobiologiques de Nancy.

In a preferred embodiment, a deodorant composition comprises one or more anti-microbial agents, such as, for example, Triclosan, and the non-aqueous silicone emulsion of the present invention In a preferred embodiment, an antiperspirant composition comprises one or more active antiperspirant agents, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, and the non-aqueous silicone emulsion of the present invention.

In a preferred embodiment, a skin cream composition comprises an emollient, such as, for example, triglyceride esters, wax esters, alkyl or alkenyl esters of fatty acids or polyhydric alcohol esters, and the non-aqueous silicone emulsion of the present invention.

In a preferred embodiment, a sunscreen composition comprises one or more absorbing or blocking agents for ultraviolet radiation, such as, for example, titanium dioxide, zinc oxide, octylcrylene, octyl methoxy cinnamate, avobenzone oxybenzone sunscreens and p-aminobenzoic acid, and the non-aqueous silicone emulsion of the present invention.

These cosmetic compositions will in all probability also contain other materials designed to improve appearance or functionality of the composition and as such cosmetic compositions prepared with the compositions of the present invention may additionally comprise such know components as, for example, emollients, pigments, colorants, fragrances, preservatives, exfoliants, hormones, enzymes, medicinal compounds, anti-microbial agents, anti-fungal agents, vitamins, salts, absorbing agents for ultraviolet (UV) radiation and botanical extracts, as well as thickening agents, such as, for example, fumed silica or hydrated silica, and clays, such as, for example, bentonite.

The respective disclosures of all United States patents referenced herein are hereby incorporated herein by reference.

EXPERIMENTAL

Example 1
Preparation of Crosslinked Silicone Polymers in Volatile, Low Molecular Weight Silicone Oil The crosslinked silicone polymers were prepared by mixing a given silyl hydride species, a given vinyl species, and a volatile low molecular weight silicone oil in a reaction vessel and mixing. To such a mixture a standard hydrosilylation catalyst was added. Hydrosilylation in the presence of platinum catalysts is described in U.S. Pat. Nos. 3,159,601; 3,159,662; 3,220,972; 3,715,334; 3,775,452; and 3,814,730 herewith and hereby incorporated by reference. The mixture containing the hydrosilylation catalyst was heated and allowed to react at a given temperature. Thus, for example, 1.11 grams of $(M^H{}_2Q)_4$, w=2, z=1, and j=4; 250 g of a vinyl terminated siloxane having an equivalent weight of 33,750 grams/equivalent vinyl, and 650 g of octamethylcyclotetrasiloxane were added to a dough mixer and stirred. 100 g of 0.11% platinum catalyst in octamethylcyclotetrasiloxane was added. The reaction was stirred and heated to 80° C. for two hours. The reaction was cooled and the product was isolated. Following this general procedure compositions A through T were prepared. The vinyl siloxane was varied through these preparations:

1) divinyl siloxane (A) is $M^{Vi}D_xM^{Vi}$ where $M^{Vi}$ is $R^1R^2R^3SiO_{1/2}$ where $R^1$ is $(CH_2=CH)$ and $R^2$ and $R^3$ are each independently $CH_3$, and D is $R^4R^5SiO_{2/2}$ where $R^4$ and $R^5$ are each independently $CH_3$, with x varied from approximately 450 to approximately 1250;

2) monovinyl siloxane (B) is $M^{Vi}D_yM$ where $M^{Vi}$ is $R^1R^2R^3SiO_{1/2}$ where $R^1$ is $(CH_2=CH)$ and $R^2$ and $R^3$ are each independently $CH_3$, D is $R^4R^5SiO_{2/2}$ where $R^4$ and $R^5$ are each independently $CH_3$, with y approximately equal to 200 and M is $R^8R^9R^{10}SiO_{1/2}$ with $R^8$, $R^9$, and $R^{10}$ each independently $CH_3$; and 3) pentavinyl siloxane (C) is $MD_iD^{Vi}{}_kM$ where M is $R^8R^9R^{10}SiO_{1/2}$ with $R^8$, $R^9$, and $R^{10}$ each independently $CH_3$, D is $R^4R^5SiO_{2/2}$ where $R^4$ and $R^5$ are each independently $CH_3$, with i approximately equal to 200, and $D^{vi}$ defined as: $D^{vi}=R^6R^7SiO_{2/2}$ where $R^6$ is $(CH_2=CH)$ and $R^7$ is independently $CH_3$, with k approximately equal to 5.

TABLE 1

Preparation of Crosslinked Polymeric Siloxane in Volatile, Low Molecular Weight Silicone Oil: $(M^H{}_2Q)_4$ Resin Reacted with Divinyl Terminated Siloxane (A)

| Comp'n | Si—H to Si-Vinyl Ratio | Divinyl Siloxane A, mol. wt. | Polymer, wt. % | Volatile, Low Mol. Wt. Silicone, wt. % | Platinum, ppm |
|---|---|---|---|---|---|
| A | 0.7/1.0 | 66800 | 25 | 75 | 10 |
| B | 0.9/1.0 | 66800 | 25 | 75 | 10 |
| C | 1.0/1.0 | 66800 | 25 | 75 | 10 |
| D | 1.1/1.0 | 66800 | 25 | 75 | 10 |
| E | 1.3/1.0 | 66800 | 25 | 75 | 10 |
| F | 1.5/1.0 | 66800 | 25 | 75 | 10 |
| G | 1.58/1.0 | 66800 | 25 | 75 | 10 |
| H | 1.3/1.0 | 33500 | 25 | 75 | 10 |
| I | 1.3/1.0 | 92700 | 25 | 75 | 10 |
| J | 1.3/1.0 | 66800 | 25 | 75* | 10 |
| U | 1.3/1.0 | 66800 | 50 | 50 | 5 |
| V | 1.3/1.0 | 66800 | 15 | 85 | 5 |

Note:
*With the exception of preparation J which utilized D5 (decamethylcyclopentasiloxane) all the other preparations utilized D4 (octamethylcyclotetrasiloxane).

Preparations A through G study variations in the hydride to vinyl ratio of the hydrosilylation reaction. Preparations E, H and I study variations in the molecular weight of the vinyl component of the hydrosilylation reaction. Preparations E and J study variations in the volatile, low molecular weight silicone oil.

The following preparations utilized a mixture of vinyl siloxane compounds, divinyl siloxane A and monovinyl siloxane B, in contrast to those preparations presented in Table 1 which utilized only one vinyl siloxane compound, divinyl siloxane A.

TABLE 2

Preparation of Crosslinked Polymeric Siloxane in Volatile, Low Molecular Weight Silicone Oil: $(M^H{}_2Q)_4$ Resin Reacted with Mixed Divinyl Terminated Siloxane (A) and Monovinyl Siloxane (B)

| Comp'n | Si—H to Si-vinyl Ratio | Divinyl Siloxane A, mol. wt. | Monovinyl Siloxane B, mol. wt. | A/B | Polymer, wt. % | Volatile, Low Mol. Wt. Silicone, wt. % | Platinum, ppm |
|---|---|---|---|---|---|---|---|
| K | 1.3/1.0 | 66800 | 15900 | 90/10 | 25 | 75 | 10 |
| L | 1.3/1.0 | 66800 | 15900 | 80/20 | 25 | 75 | 10 |

TABLE 2-continued

Preparation of Crosslinked Polymeric Siloxane in Volatile, Low Molecular Weight Silicone Oil: $(M^H{}_2Q)_4$ Resin Reacted with Mixed Divinyl Terminated Siloxane (A) and Monovinyl Siloxane (B)

| Comp'n | Si—H to Si-vinyl Ratio | Divinyl Siloxane A, mol. wt. | Monovinyl Siloxane B, mol. wt. | A/B | Polymer, wt. % | Volatile, Low Mol. Wt. Silicone, wt. % | Platinum, ppm |
|---|---|---|---|---|---|---|---|
| M | 1.3/1.0 | 66800 | 15900 | 70/30 | 25 | 75 | 10 |
| N | 1.3/1.0 | 66800 | 15900 | 60/40 | 25 | 75 | 10 |
| O | 1.3/1.0 | 66800 | 15900 | 50/50 | 25 | 75 | 10 |
| P | 1.1/1.0 | 66800 | 15900 | 90/10 | 25 | 75 | 10 |
| Q | 1.1/1.0 | 66800 | 15900 | 70/30 | 25 | 75 | 10 |
| R | 1.1/1.0 | 66800 | 15900 | 50/50 | 25 | 75 | 10 |

Preparations K through O vary the ratio of divinyl siloxane A to mono-vinyl siloxane B at a constant hydride to vinyl ratio. Preparations P through R again vary the ratio of divinyl siloxane A to mono-vinyl siloxane B but at a different constant hydride to vinyl ratio from that in K through O.

The following preparations utilized a mixture of vinyl siloxane compounds, divinyl siloxane A and pentavinyl siloxane C, in contrast to those preparations presented in Table 1 which utilized only one vinyl siloxane compound, divinyl siloxane A.

TABLE 3

Preparation of Crosslinked Polymeric Siloxane inn Volatile, Low Molecular Weight Silicone Oil: $(M^H{}_2Q)_4$ Resin Reacted with Mixed Divinyl Terminated Siloxane (A) and Pentavinyl Siloxane (C)

| Comp'n | Si—H to Si-Vinyl Ratio | Divinyl Siloxane A, mol. wt. | Pentavinyl Siloxane B, mol. wt. | A/B | Polymer, wt. % | Volatile, Low Mol. Wt. Silicone, wt. % | Platinum, ppm |
|---|---|---|---|---|---|---|---|
| S | 1.3/1.0 | 66800 | 16200 | 90/10 | 25 | 75 | 10 |
| T | 1.3/1.0 | 66800 | 16200 | 80/20 | 25 | 75 | 10 |

The preparations reported in Table 3 vary the mixture of vinyl siloxanes being used to prepare the crosslinked material from that reported in Table 2.

Example 2
Dilution of Crosslinked Gels with Volatile, Low Molecular Weight Silicone Oils The crosslinked gels prepared in example 1 were further diluted with volatile, low molecular weight silicone oils to produce a slurry. The volatile, low molecular weight silicone oils used for dilution were either the same as that used to prepare the crosslinked gel or different. The slurry was subjected to shearing forces in a homogenizer to produce a clear product of a desired viscosity for a specific cosmetic application. The viscosity of the gel volatile slurry that had been subjected to shearing forces ranged from about 100 centistokes to over about 100,000 centistokes at 25° C. Thus for example, 400 g of preparation E was blended with 1,600 g of $D_4$, octamethylcyclotetrasiloxane. Preparation E contains 25 wt. % crosslinked polymer, i.e. 100 g, and therefore the slurry of E in $D_4$ is 5 weight percent polymer. The mixture of 5 percent by weight ("wt. %") crosslinked polymer in $D_4$ was passed through a Gaulin homogenizer at 7,000 psi pressure. The resulting material was clear and had a viscosity of 120,000 centistokes at 25° C. The preparation of other material according to this general procedure is reported in Table 4.

TABLE 4

Viscosity of Sheared Crosslinked Silicone Polymers Diluted to 5 Wt. %

| Comp'n | Table 1 Gel | Wt. % Gel | Wt. % Volatile, Low Molecular Weight Silicone | Viscosity, cps at 25° C. |
|---|---|---|---|---|
| AA | A | 5 | 95 | 28,400 |
| BB | B | 5 | 95 | 35,300 |
| CC | C | 5 | 95 | 61,800 |
| DD | D | 5 | 95 | 74,100 |
| EE | E | 5 | 95 | 115,000 |
| FF | F | 5 | 95 | 110,000 |
| GG | G | 5 | 95 | 112,000 |
| HH | H | 5 | 95 | 47,300 |
| II | I | 5 | 95 | 31,400 |
| JJ | J | 5 | 95 | 80,000 |
| KK | K | 5 | 95 | 72,700 |
| LL | L | 5 | 95 | 49,000 |
| MM | M | 5 | 95 | 27,200 |
| NN | N | 5 | 95 | 8,600 |
| OO | O | 5 | 95 | 2,500 |
| PP | P | 5 | 95 | 49,000 |
| QQ | Q | 5 | 95 | 22,000 |
| RR | R | 5 | 95 | 1,800 |
| SS | S | 5 | 95 | 81,700 |
| TT | T | 5 | 95 | 93,100 |
| UU | U | 6 | 94 | 20,000 |
| VV | V | 3.5 | 96.5 | 122,000 |

These data indicate that:
1) as hydride to alkenyl (vinyl) ratio is changed through 0.7 to 1.6 (hydride) to 1.0 (alkenyl) the product gel viscosity increases;
2) as the molecular weight of the alkenyl component increases, extending the distance between crosslink sites,
   i) the ability of the initially produced polymer gel to swell upon the addition of volatile silicones increases and
   ii) the viscosity increases; and
3) increasing the average functionality of the alkenyl precursor from 1.3 to 2.0, increases the crosslink density and the viscosity of the resulting product.

Example 3
Comparison of Low Crosslink Density Gels with High Crosslink Density Gels The processed gels of the present invention are gels that have a high crosslink density, due to the use of the $M^HQ$ resin and vinyl siloxanes that a fairly low equivalent weight with respect to the vinyl group. For purposes of comparison, gels possessing a low density crosslinking network were prepared. Thus, the procedures outline to prepare the gels of example one were utilized with a linear hydride siloxane containing only two equivalents of hydride per molecule and a vinyl siloxane containing only two equivalents of vinyl per molecule (on average). Thus 2.02 g of a hydrogen terminated siloxane having a molecular weight of about 1,818 and 75 g of a vinyl terminated siloxane having a molecular weight of 67,500 were mixed with 425 g of octamethylcyclotetrasiloxane. The mixture was stirred and 10 ppm platinum catalyst was added as previously described. The mixture was heated to 80° C. for five hours. The product was cooled and isolated. The viscosity was 88.5 centistokes at 25° C. The results demonstrate that siloxane polymers made from low functionality ingredients produce siloxane polymers with little crosslinking and thus low efficiency in controlling the viscosity of the volatile siloxanes.

Elastomer Solids Content

The percent solid elastomer in the product was determined by placing a weighed sample in an oven at 150° C. for 45 minutes and observing the weight loss.

Viscosity

The elastomer/volatile siloxane solutions after processing under flow induced shear and elongation where evaluated for viscosity 24 hours after the processing sample was taken on a Brookfield RVT Viscometer with a T-C spindle at 4 RPM.

Aesthetic Evaluation

Elastomer/volatile siloxane samples were evaluated for the presence of "gel balls" by applying a small sample to the skin and rubbing until the solvent spread and evaporated. During this process the presence of very small, undesirable balls of silicone were observed in incompletely processed material.

Particle Size

The particle size analysis was done using a Malvern Mastersizer™ fitted with a 300 mm lens. Applicants note that the particle sizes determined will vary as a function of the different type of apparatus used to determine the particle size. Thus, while a particle size appears intrinsically to be absolutely determinable, it is in fact governed by the machine used to measure it. Accordingly, the particle sizes herein recited are those determined by a Malvern Mastersizer and should other machines by used by other practitioners, those machines must be referenced or calibrated against the sizes as determined by a Malvern Mastersizer. The desired material (10 grams) generally containing 5 to 10% elastomer swollen with 90–95% cyclic siloxanes was dissolved in a 50/50 mixture (40 grams) of isopropanol (IPA) and decamethylcyclopentasiloxane (D5). This solution was then added to approximately 500 grams of a 50/50 IPA/D5 that had already been placed in the reservoir of the Malvern Mastersizer. The resulting solution was circulated through the instrument for five minutes and then triplicate measurements were taken. The limits on the Malvern Mastersizer extend from 1 to 600 microns with the 300 mm lens. A 45 mm lens was also employed to look for smaller particles with no significant number being found. Particles greater than 600 microns such as those that might cause gel balls were not visible by this method.

Earlier experiments have shown that the particles prepared in this invention are not fully swollen in material as dilute as five percent elastomer content and 95% cyclic siloxanes. However, if the elastomer is further diluted below elastomer contents of about three percent, the particle swells to its full extent. Thus the particle sizes measured in this experiment demonstrate fully extended particles, while those used in most applications are of proportionally smaller actual volume depending on the available solvent. Since for a given particle composition it is possible to measure how much additional solvent may be absorbed, it is possible to back calculate the particle size for any given concentration once the full extended particle size is known. Further, it is within the scope of this invention to prepare smaller particles at a higher elastomer concentration and then swell them at a later time with additional solvent to achieve a larger particle size.

Example 4
Preparation of Elastomer Samples

The elastomer samples were prepared by mixing the low molecular weight, volatile siloxane, vinylsiloxane and silylhydride together and mixing. This was followed by platinum catalyst addition and slow heating to 80° C. to allow cure of the elastomer. This was done with stirring to promote breaking of the resulting elastomer into pieces to accommodate the ensuing processing steps.

Thus in a typical example 7.28 gm. of $[(HMe_2SiO)_2SiO]_4$ with 0.92% hydride content, 1500 gm. of vinyl terminate polysiloxane containing 0.089% vinyl and 4500 gm. of decamethylcyclopentasiloxane were added to a 10 l Drais mixer and allowed to mix at 20° C. Platinum catalyst was then added and the temperature slowly brought to 80° C. and held for two hours. The product was then removed from the Drais and used in the following examples.

Example 5
Dilution

The 25% elastomer/volatile siloxane produced above was further diluted with the same or a different low molecular weight siloxane before being subjected to high, flow induced shear and elongation. Generally the 25% elastomer/volatile siloxane was diluted to about 5 to 7% solid elastomer content in order to facilitate processing and introduce additional stress to the crosslinked polysiloxane particle.

In a typical example 450 gm. of 25% elastomer/volatile siloxane was added to 1550 gm. of decamethylcyclopentasiloxane and allowed to swell before processing. After processing the solution was checked for solid elastomer content by the method described above and found to be 5.62%.

Example 6
Sonolator Processed Material

The diluted solution of elastomer/volatile siloxane was fed to the Sonolator unit by a pump such that a constant pressure was maintained on the orifice. Orifice size was varied through the experiments. Through-put was then measured to determine flow. Processing was done either in discreet passes or by recycling to the feed chamber with the number of passes being determined by the through-put and processing time. Samples were taken directly from the end of the sample loop at desired intervals.

Gaullen Homogenizer

The Gaullen Homogenizer was run in a manner similar to the Sonolator with respect to feeds, discreet passes and number of passes with time for extended samples. The pressure measurement was taken from the pressure measured in the feed chamber controlled by the pressure setting on the orifice pin.

Microfluidizer

The microfluidizer was generally fed material previously diluted and reduced in particle size from well over 1 mm to an average of about 1000 microns with a rotor/stator mixer. Material was then pumped through the Microfluidizer in discreet passes. The Microfluidizer was run using two chambers. In all cases the first was a H30Z chamber and the second either a J30Y or a smaller J20Y chamber.

Pressure Related Experiments

A.) The 25% elastomer/volatile siloxane product made above was diluted to approximately 5.5% solid elastomer content with pentamethylcyclopentasiloxane. The material was cycled through a Sonolator at 300 psi and sampled as follows:

| Passes | 11.25 | 33.75 | 56 | 112 |
|---|---|---|---|---|
| Viscosity | 23150 | 23450 | 22450 | 20100 |
| Aesthetics | Gel Balls | Gel Balls | Gel Balls | Gel Balls |

The experiment shows that at low pressure over a very extended number of cycles the material did not break into sufficiently small particles to form an aesthetically acceptable material of high viscosity.

B.) Similarly, 25% elastomer/volatile siloxane was diluted to 5.62% using decamethylcyclopentasiloxane. The material was processed through the Sonolator at 1000 psi and samples taken as follows:

| Passes | 18 | 30 |
|---|---|---|
| Viscosity | 40000 | 33000 |
| Aesthetics | Slight Gel Balls | No Gel Balls |
| Particle Size | | |
| Peak Center and Volume Area Percent | | |
| 23.5 micron | 0.50% | 2.54% |
| 36.5 | 8.04 | 19.23 |
| 53.0 | 24.23 | 31.93 |
| 65.1 | | 46.30 |
| 71.7 | 66.52 | |

C.) A 25% elastomer/volatile siloxane made in the manner stated above was diluted to 5.5% with decamethylcyclopentasiloxane. The material was processed through a Sonolator at 4500 psi and samples taken as follows:

| Passes | 3 | 4 |
|---|---|---|
| Viscosity | | |
| Aesthetics | No Gel Balls | No Gel Balls |
| Particle Size | | |
| Peak Center and Volume Percent | | |
| 13.4 microns | 0.08% | 0.28% |
| 23.3 | 3.70 | 9.11 |
| 36.2 | 9.37 | 9.14 |
| 52.0 | 12.46 | 18.31 |
| 71.5 | 74.40 | |
| 75.0 | | 63.16 |

Experiments 6 A, B and C show that increasing the flow induced shear and elongation by increasing pressure provides a significantly faster and more economic (fewer passes to achieve acceptable aesthetics) method for processing the crosslinked polysiloxane. At the same time the product viscosity is dramatically higher in high flow induced shear and elongation samples which is a distinct advantage in requiring lower amounts of crosslinked polysiloxane in formulated products where maintaining a high viscosity cream is important. The particle size comparison of examples 6 B and C shows that the material made with 3 passes at high flow induced shear and elongation has a broader distribution of particle sizes (more large particles and more small particles) than a comparable sample made at lower flow induced shear and elongation. The result of this is that the high flow induced shear and elongation sample has an advantage in containing both higher viscosity from large particle sizes and smoother feel during application to the skin from the small particle sizes.

Example 7

A.) A 25% elastomer/volatile siloxane sample prepared as described above was diluted to 5% with an 85/15 blend of octamethylcyclotetrasiloxane and decamethylcyclopentasiloxane. The material was processed in the Gaullin Homogenizer as described above at 4000 psi and sampled as follows:

| Passes | 11 | 45 |
|---|---|---|
| Viscosity | 2640 | 20300 |
| Aesthetics | Gel Balls | Few Gel Balls |
| Particle Size | | |
| Peak Center and Volume Percent | | |
| 23.3 | | 4.32 |
| 36.2 | | 11.88 |
| 54.3 | | 28.56 |
| 88.3 | | 55.23 |

B.) A 25% elastomer/volatile siloxane sample prepared as described above was diluted to 5% with an 85/15 blend of octamethylcyclotetrasiloxane and decamethylcyclopentasiloxane. The material was processed in the Gaullin Homogenizer as described above at 7000 psi and sampled as follows:

| Passes | 5 |
|---|---|
| Viscosity | 78100 |
| Aesthetics | No Gel Balls |
| Particle Size | |
| Peak Center and Volume Percent | |
| 23.3 | 5.73 |
| 36.2 | 7.48 |
| 52.0 | 20.26 |
| 88.4 | 66.52 |

Comparison of examples 7 A and B shows that as the flow induced shear and elongation is increased by increasing the pressure, the number of passes required to make acceptable product free of gel balls is significantly reduced. In addition, with higher flow induced shear and elongation higher viscosity is obtained. Comparison of the particle size after 5 passes at high flow induced shear and elongation is broader than after 45 passes at low flow induced shear and elongation. The result is advantageous in providing higher viscosity from large particles and superior feel and flow characteristics from low particle sizes.

Example 8

A.) A 25% elastomer/volatile siloxane sample prepared as described above was diluted to 5% with an 85/15 blend of octamethylcyclotetrasiloxane and decamethylcyclopentasiloxane. The material was processed in the Microfluidizer at 6,000 psi with a sample taken as follows:

| Passes | 1 |
|---|---|
| Viscosity | <10,000 |
| Aesthetics | Gel Balls |

B.) A 25% elastomer/volatile siloxane sample prepared as described above was diluted to 5% with an 85/15 blend of octamethylcyclotetrasiloxane and decamethylcyclopentasiloxane. The material was processed in the Microfluidizer at 18,000 psi with a sample taken as follows:

| Passes | 1 |
|---|---|
| Viscosity | >60,000 |
| Aesthetics | No Gel Balls |

C.) A 25% elastomer/volatile siloxane sample prepared as described above was diluted to 5% with an 85/15 blend of octamethylcyclotetrasiloxane and decamethylcyclopentasiloxane. The material was processed in the Microfluidizer at 16,000 psi with the larger J30Y chamber and a sample taken as follows:

| Passes | 1 |
|---|---|
| Viscosity | 84400 |
| Aesthetics | No Gel Balls |
| Particle Size | |
| Peak Center and Volume Percent | |
| 24.3 | 1.49 |
| 36.1 | 3.91 |
| 51.3 | 6.98 |
| 71.2 | 34.58 |
| 117.7 | 53.03 |

Example 8 A, B and C shows that as flow induced shear and elongation is increased by increasing the pressure in a Microfluidizer, the product is more efficiently processed to aesthetically acceptable material having the desired high viscosity. The high flow induced shear and elongation also provides a broad particle size distribution.

Orifice Size Related Experiments

Example 9

A.) A 25% elastomer/volatile siloxane sample prepared as described above was diluted to 5% with an 85/15 blend of octamethylcyclotetrasiloxane and decamethylcyclopentasiloxane. The material was processed in the Microfluidizer at 16,000 psi with a smaller J20Y chamber and a sample taken as follows:

| Pass | 1 |
|---|---|
| Viscosity | 172750 |
| Aesthetics | No Gel Balls |
| Particle Size | |
| Peak Center and Volume Percent | |
| 23.5 | 0.12 |
| 35.8 | 0.62 |
| 51.9 | 2.83 |
| 72.7 | 5.10 |
| 132.7 | 91.33 |

The comparison of example 9 and example 8 C shows that decreasing the orifice size while maintaining pressure diminishes the breadth of particle size distribution.

Example 10

A.) A 25% elastomer/volatile siloxane made in the manner stated above was diluted to 5.5% with decamethylcyclopentasiloxane. The material was processed through a Sonolator at 4500 psi with a 0.0021 orifice size and samples taken as follows:

| Pass | 1 |
|---|---|
| Viscosity | NA |
| Aesthetics | Gel Balls |
| Particle Size | |
| Peak Center and Volume Percent | |
| 23.4 | 0.69 |
| 35.8 | 2.16 |
| 56.7 | 15.72 |
| 111.5 | 81.43 |

B.) A 25% elastomer/volatile siloxane made in the manner stated above was diluted to 5.5% with decamethylcyclopentasiloxane. The material was processed through a Sonolator at 4500 psi with a 0.0008 orifice size and samples taken as follows:

| Pass | 1 |
|---|---|
| Viscosity | NA |
| Aesthetics | Gel Balls |
| Particle Size | |
| Peak Center and Volume Percent | |
| 23.4 | 0.39 |
| 35.8 | 1.63 |
| 60.7 | 22.21 |
| 111.5 | 75.77 |

Example 11

A.) A 25% elastomer/volatile siloxane made in the manner stated above was diluted to 5.5% with decamethylcyclopentasiloxane. The material was processed through a Sonolator at 4500 psi with a 0.0021 orifice size and samples taken as follows:

| Passes | 2 |
|---|---|
| Particle Size | |
| Peak Center and Percent Volume | |
| 23.5 | 1.32 |
| 36.4 | 4.35 |
| 51.8 | 7.90 |
| 71.5 | 20.06 |
| 118.9 | 66.36 |

B.) A 25% elastomer/volatile siloxane made in the manner stated above was diluted to 5.5% with decamethylcyclopentasiloxane. The material was processed through a Sonolator at 4500 psi with a 0.0008 orifice size and samples taken as follows:

| Passes | 2 |
|---|---|
| Particle Size | |
| Peak Center and Volume Percent | |
| 23.4 | 1.39 |
| 36.4 | 4.62 |
| 52.0 | 7.84 |

-continued

| Passes | 2 |
|---|---|
| 71.4 | 21.09 |
| 120.0 | 65.05 |

Examples 10 A and B demonstrate the broader particle size distribution achieved with a wider orifice size. In these examples the crosslinked elastomer was not subjected to sufficient shear to achieve the desired aesthetic standard of no gel balls, and further passes were done. As further passes were made, examples VIII A and B, the particle size distribution for each orifice size became similar as the result of randomization of the position of the particles as they went through the orifice. In general the effects on particle size distribution of orifice size are less pronounced in the Sonolator than in the Microfluidizer reflecting the shorter orifice path length. Because of the shorter path length in the Sonolator, more of the flow induced shear and particle elongation is created as the material is compacted before entering the orifice. Since this is similar for both orifice sizes, the change with orifice size is less dramatic.

Viscosity Related Experiments

Example 12

A 25% elastomer/volatile siloxane made in the manner stated above was diluted to 5.5% with decamethylcyclopentasiloxane. 10 weight % of 350 cps viscosity polydimethylsiloxane was added and mixed in. The polydimethylsiloxane oil was observed not to completely penetrate the crosslinked polysiloxane elastomer, but rather to coat the surface causing a dramatic reduction in viscosity. This viscosity lowering was observed through the entire processing step.

The material was processed through a Sonolator with a 0.0008 orifice at 1000 psi and samples taken as follows:

| Passes | 11 | 22 | 34 | 45 | 56 |
|---|---|---|---|---|---|
| Viscosity | 400 | 400 | 400 | 400 | 400 |
| Aesthetics | Gel Balls | Gel Balls | No Gel Balls | | |
| Particle Size Peak Center and Volume Percent | | | | | |
| 12.8 | 0 | 0 | 0 | 0 | 0 |
| 23 | 0.05 | 0.18 | 0.40 | 0.33 | 0.22 |
| 36 | 0.58 | 1.83 | 3.52 | 4.03 | 4.50 |
| 56 | | 22.79 | 18.11 | 10.03 | 7.27 |
| 64 | 14.58 | | | | |
| 75 | | | | 85.60 | 88.01 |
| 90 | | | 77.98 | | |
| 99 | | 75.20 | | | |
| 140 | 84.79 | | | | |

Comparison of example 12 with example 6 B run at the same pressure, demonstrates that viscosity is critical in producing the particle size range. Thus when the viscosity is reduced to about 400 ctks., particles sizes remain too large through more cycles and only very slowly produce particles of small size. At low viscosity there is lower flow induced shear and elongation to break up the particles.

Particle Size Distribution Characterization Experiments

In the preparation of the material of the present invention by the process of the present invention, depending on the number of passes at a given pressure, material possessing the three particle size ranges defined as necessary for the compositions of the present invention can be prepared in proportions of those particle size ranges that differ and therefore provide subjective differences in feel.

Large Average Particle Size
Particle Size Distribution: Material Ranging from about 100 to 600 microns

| Average Particle Size of Population microns | 10–15 | 21–26 | 33–38 | 50–60 | 65–80 | 100 to 300 |
|---|---|---|---|---|---|---|
| Volume % Range | 0 | 0.1–2 | 0.1–5 | 1.0–10 | 10–50 | 40–95 |
| Peak Width at Half-Height | 0 | 0.1–10 | 1–10 | 10–30 | 25–100 | 75–200 |

The material having a large average particle size from 100 to 600 microns has a thick consistency much like commercial gelatin food products. When applied to the skin, the material is hard to rub into the skin, sticks to itself rather than spreading onto the skin and does not readily wet the skin and form a thin film.

Moderate Average Particle Size
Particle Size Distribution: Material Ranging from about 50 to 150 microns

| Average Particle Size of Population microns | 10–15 | 21–26 | 33–38 | 50–60 | 65–80 | 100 to 300 |
|---|---|---|---|---|---|---|
| Volume % Range | 0.1–5 | 1–5 | 5–20 | 10–35 | 30–80 | 0–20 |
| Peak Width at Half-Height | 0.1–3 | 1–15 | 5–20 | 15–40 | 40–125 | 75–200 |

The material having a moderate average particle size ranging form 50 to 150 microns has a smooth creamy pudding-like consistency. When applied to the skin, the material exhibits some resistance when rubbed on the skin producing a cushion or sponge like feel that that conveys a subjective perception of a rich fullness.

Small Average Particle Size
Particle Size Distribution: Material Ranging from about 10 to 100 microns

| Average Particle Size of Population microns | 10–15 | 21–26 | 33–38 | 50–60 | 65–80 | 100 to 300 |
|---|---|---|---|---|---|---|
| Volume % Range | 5–15 | 15–60 | 20–50 | 1–30 | 0 | 0 |
| Peak Width at Half-Height | 2–15 | 3–20 | 5–25 | 5–30 | 0 | 0 |

The material having a small average particle size has a thin fluid like consistency. When applied to the skin this material spreads readily across the skin with little or no resistance and produces an initial heavy or greasy feel. However, once applied to the skin, this material provides a smooth silky feel on the skin.

It should be noted that all three of the foregoing examples of a controlled particle size composition possess the specific particle sizes characteristically produced by the process.

Preparation of Non-Aqueous Silicone Emulsions

Example 13

A transparent gel anhydrous emulsion useful as an antiperspirant or deodorant was prepared by blending together two mixtures A and B that respectively had the following composition:

| Material | Weight Percent |
| --- | --- |
| Part A: | |
| Solution of 40.0 wt. % dimethicone copolyol in cyclomethicone | 2.5 |
| Swollen elastomer (elastomer gel swollen with cyclomethicone, as in example 12) | 7.0 |
| Phenyl trimethicone | 14.5 |
| Part B: | |
| Polysorbate 80 ® | 0.25 |
| Propylene glycol | 47.42 |
| 30% ZAC in propylene glycol | 23.33 |
| Ethanol | 5.00 |

The preparation was accomplished as follows:

1) the ingredients comprising part A were mixed together;
2) reserving 3 percent of the propylene glycol for later use, the Polysorbate 80® and ethanol were dissolved in the propylene glycol;
3) the ZAG solution in propylene glycol (30 wt. % aluminum zirconium pentachlorohydrex GLY) was added to the Polysorbate 80® and ethanol propylene glycol solution;
4) the refractive indices of both parts A and B were measured and adjusted using liquids of different refractive index such that the refractive index of part B was matched to the refractive index of part A to within 0.00010 RI units;
5) part B was slowly added to part A once the desired match in refractive index was achieved using moderate shear mixing which was gradually increased as the mixture thickened and agitation was continued in this fashion for fifteen minutes; and
6) homogenize for approximately two minutes with a high speed high shear mixer such as an Eppenbach™ mixer.

The purpose of matching the refractive index of the two phases comprising the emulsion is to prepare an emulsion that is transparent to the naked eye, irrespective of the particle sizes of the dispersed phase. Thus by matching the refractive indices of the two immiscible phases, embodiments of the present invention that are transparent may be prepared. This may be accomplished by the addition of suitable liquid components to either phase that have, as appropriate, either higher or lower indices of refraction.

Examples 14 and 15

The procedure of example 13 was followed using:

| Material | Weight Percent |
| --- | --- |
| Part A: | |
| Solution of 40.0 wt. % dimethicone copolyol in cyclomethicone | 2.5 |
| Swollen elastomer (elastomer gel swollen with cyclomethicone, as in example 12) | 7.0 |
| Phenylpropyl siloxane | 14.5 |
| Part B: | |
| Polysorbate 80 ® | 0.25 |
| Propylene glycol | 55.75 |
| 35% ZAG4 (35 wt. % aluminum zirconium tetrachlorohydrex GLY) in propylene glycol | 20.00 |

After the addition of part B to part A the sample was split into two more or less equal fractions, example 14 was not homogenized while example 15 was homogenized for approximately 2 minutes using the Eppenbach™ homogenizer. The materials as prepared were measured for viscosity using a Brookfield viscometer at 25° C., tested for stability at room temperature, at 40° C., and under freeze-thaw conditions. Table 5 shows the viscosities and stabilities.

TABLE 5

Comparative Viscosities and Stabilities of Homogenized and Un-Homogenized Non-Aqueous Emulsions

| | Example 14 | Example 15 |
| --- | --- | --- |
| Homogenized | No | Yes |
| Initial Viscosity, cps at 25° C. | 26,000 | 64,500 |
| Viscosity after 5 freeze thaw cycles, cps at 25° C. | 27,000 | 64,500 |
| Stability at Room Temperature, 1 month | unchanged | unchanged |
| Stability at Room Temperature, 2 months | unchanged | unchanged |
| Stability at 40° C., 1 month | unchanged | unchanged |
| Stability at 40° C., 2 months | unchanged | unchanged |
| Stability after 10 freeze thaw cycles | flowable but not separated | unchanged |

These examples demonstrate that emulsions of the present invention are stable irrespective of whether high shear homogenization is employed in the preparation.

Example 16

The procedure of example 13 was followed using:

| Material | Weight Percent |
| --- | --- |
| Part A: | |
| Solution of 40.0 wt. % dimethicone copolyol in cyclomethicone | 2.5 |
| Swollen elastomer (elastomer gel swollen with cyclomethicone) | 0.0 |
| Cyclomethicone | 7.0 |
| Phenylpropyl siloxane | 14.5 |

| Material | Weight Percent |
|---|---|
| Part B: | |
| Polysorbate 80 ® | 0.25 |
| Propylene glycol | 55.75 |
| 35% ZAG4 in propylene glycol | 20.00 |

TABLE 6

Comparative Viscosities and Stabilities of Homogenized Non-Aqueous Emulsions With and Without Swollen Elastomer Gel

| | Example 16 | Example 15 |
|---|---|---|
| Swollen Elastomer Gel | No | Yes |
| Initial Viscosity, cps at 25° C. | 31,000 | 64,500 |
| Viscosity after 5 freeze thaw cycles, cps at 25° C. | 22,000 | 64,500 |
| Stability at Room Temperature, 1 month | unchanged | unchanged |
| Stability at Room Temperature, 2 months | unchanged | unchanged |
| Stability at 40° C., 1 month | unchanged | unchanged |
| Stability at 40° C., 2 months | unchanged | unchanged |
| Stability after 10 freeze thaw cycles | flowable but not separated | unchanged |

Material Descriptions

1. Cyclomethicone is a mixture of volatile cyclic dimethyl siloxanes having the general formula $((CH_3)_2SiO)_x$ where x ranges from 3 to 6.
2. Dimethicone copolyol is a copolymeric siloxane that is polyoxyalkylene modified having the formula $MD500D'6.5M$ where $M=((CH_3)_3SiO_{1/2}$, $D=(CH_3)_2SiO_{2/2}$ and $D'=(CH_3)SiO((OC_2H_4)_{20.5}(OC_3H_6)_{15.5}OH$.
3. Phenyltrimethicone is $(C_6H_5)Si(OSi(CH_3)_3)_3$.
4. Phenylpropyl siloxane is $M'D_3M'$ where $M'$ is $((C_6H_5)CH(CH_3)CH_2)(CH_3)_2SiO_{1/2}$ and D is as defined above for dimethicone copolyol or $MD"M$ where M is as defined above for dimethicone copolyol and $D"$ is $((C_6H_5)CH(CH_3)CH_2)(CH_3)SiO_{2/2}$.
5. Swollen elastomer gel (the silicone composition of the instant invention) is the addition product of $M^{Vi}_aD_xD^{vi}_yM_{2-a}$ and $(M^H_wQ_z)_j$ in the presence of a second silicone having a viscosity below about 1,000 centistokes at 25° C. where the addition product is a gel and particle size distribution of the gel is controlled and comprises:
   a) a local maximum ranging from about 21 to about 26 microns;
   b) a local maximum ranging from about 33 to about 38 microns,
   c) and a local maximum ranging from about 50 to 60 microns.

These examples demonstrate that emulsions that do not contain the swollen elastomer dispersion do not possess freeze thaw stability.

Examples 17 and 18

A transparent solid anhydrous emulsion useful as an antiperspirant was prepared by blending together two mixtures A and B that respectively had the following composition:

| Material | Weight Percent |
|---|---|
| Part A: | |
| Solution of 40.0 wt. % dimethicone copolyol in cyclomethicone | 2.5 |
| Swollen elastomer, marketed as "Gransil ™" (elastomer gel swollen with cyclomethicone, as described in U.S. Pat. No. 5,571,853) | 7.0 |
| Phenylpropyl siloxane | 14.5 |
| Part B: | |
| Polysorbate 80 ® | 0.25 |
| Propylene glycol | 55.75 |
| 35% ZAG4 in propylene glycol | 20.00 |

The preparation was accomplished as follows:
1) the ingredients comprising part A were mixed together;
2) reserving 3 percent of the propylene glycol for later use, the Polysorbate 80® and ethanol were dissolved in the propylene glycol;
3) the ZAG solution in propylene glycol was added to the Polysorbate 80® and ethanol propylene glycol solution;
4) the refractive indices of both parts A and B were measured and adjusted using liquids of different refractive index such that the refractive index of part B was matched to the refractive index of part A to within 0.00010 RI units;
5) part B was slowly added to part A once the desired match in refractive index was achieved using moderate shear mixing which was gradually increased as the mixture thickened and agitation was continued in this fashion for fifteen minutes; and
6) homogenize for approximately two minutes with a high speed high shear mixer such as an Eppenbach™ mixer.

After the addition of part B to part A the sample was split into two more or less equal fractions, example 17 was not homogenized while example 18 was homogenized for approximately 2 minutes using the Eppenbach™ homogenizer. The materials as prepared were measured for viscosity using a Brookfield viscometer at 25° C., tested for stability at room temperature, at 40° C., and under freeze-thaw conditions. Table 7 shows the viscosities and stabilities.

TABLE 7

Comparative Viscosities and Stabilities of Homogenized and Un-Homogenized Non-Aqueous Emulsions

| | Example 17 | Example 18 |
|---|---|---|
| Homogenized | No | Yes |
| Initial Viscosity, cps at 25° C. | 17,000 | 28,000 |
| Viscosity after 5 freeze thaw cycles, cps at 25° C. | 17,000 | 28,000 |
| Stability at Room Temperature, 1 month | N/A | N/A |
| Stability at Room Temperature, 2 months | N/A | N/A |
| Stability at 40° C., 1 month | N/A | N/A |
| Stability at 40° C., 2 months | N/A | N/A |
| Stability after 10 freeze thaw cycles | no change in viscosity | no change in viscosity |

These examples demonstrate that a swollen elastomer enables preparation of a non-aqueous emulsion irrespective of the components used to prepare the elastomer.

Example 19

The procedure of example 13 was followed with the exception of step 6, homogenization, using:

| Material | Weight Percent |
|---|---|
| Part A: | |
| Solution of 40.0 wt. % dimethicone copolyol in cyclomethicone | 2.5 |
| Cyclomethicone | 7.0 |
| Phenylpropyl siloxane | 14.5 |
| Part B: | |
| Polysorbate 80 ® | 0.25 |
| Propylene glycol | 55.75 |
| 35% ZAG4 in propylene glycol | 20.00 |

The material prepared in example 19 separated into three immiscible liquid layers after one freeze thaw cycle. These results demonstrate that dispersions of silicone elastomers in a carrier solvent stabilize non-aqueous emulsions. Further, these results indicate that the stabilizing effect of the elastomer dispersion is not dependent upon the precursor alkenyl siloxane and organohydrogen siloxane compounds used to prepare the elastomer.

As non-limiting examples of a base compositions comprising the emulsions of the present invention whereby cosmetic, personal care and drug delivery system compositions could be prepared, the following examples are presented by comparison to similar preparations that do not contain the non-aqueous emulsion stabilizing elastomer gel.

Examples 20 and 21

| Component | Example 20 | Example 21 |
|---|---|---|
| Part A | | |
| Solution of 10.0 wt. % dimethicone copolyol in cyclomethicone, parts by weight | 20.0 | 20 |
| Cyclomethicone, parts by weight | 12.5 | 0 |
| Elastomer gel swollen with cyclomethicone, parts by weight | 0 | 12.5 |
| Part B | | |
| Propylene glycol, parts by weight | 67.5 | 67.5 |

The materials of examples 20 and 21 were mixed together as follows:
1) the ingredients of part A were mixed together; and
2) part B was slowly added to part A using moderate shear mixing.

The materials as prepared were measured for viscosity using a Brookfield viscometer at 25° C. and tested for stability at room temperature, 40° C., and under freeze thaw conditions. Examples 20 and 21 as prepared are cloudy or translucent, indicating they are both emulsions. This is indicative that the propylene glycol and silicone have formed an emulsion consisting of a continuous and a discontinuous phases and both phases are non-aqueous. Table 8 shows the viscosities and stabilities.

TABLE 8

Comparison of Non-Aqueous Emulsion Cosmetic Base with and without Elastomer Gel Swollen by Silicone Oil

| Property | Example 20 | Example 21 |
|---|---|---|
| Elastomer Gel swollen with silicone oil, present? | No | Yes |
| Viscosity, initial, cps at 25° C. | 2,800 | 8,600 |
| Stability, room temperature, 3 days | separated into two layers | homogeneous emulsion, unchanged |
| Stability at 40° C., 7 days | separated into two layers | homogeneous emulsion, unchanged |
| Stability after 3 freeze thaw cycles | separated into two layers | homogeneous emulsion, unchanged |
| Viscosity after 3 freeze thaw cycles | N/A | 3,300 |

The incorporation of the silicone oil swollen silicone elastomer enables the preparation of stable non-aqueous emulsions of other silicones with non-aqueous organic hydroxylic solvents and serves to provide a basic composition useful as a base for a variety of cosmetic and personal care compositions as well as providing a component for topical drug delivery systems. The stability is improved by preservation of the emulsion over three freeze thaw cycles in contrast to the preparation where the elastomer was absent. The stability is improved by preservation of the emulsion against separation into distinct liquid phases for a period of at least three days at room temperature, and a period of at least seven days at 40° C. Thus stability is herein defined as no visible phase separation of the immiscible phases after a given period of time at a given temperature, i.e. a matter of days at a given temperature.

Examples 22 and 23

| Component | Example 22 | Example 23 |
|---|---|---|
| Part A | | |
| Solution of 10.0 wt. % dimethicone copolyol in cyclomethicone, parts by weight | 20.0 | 20 |
| Cyclomethicone, parts by weight | 12.5 | 0 |
| Elastomer gel swollen with cyclomethicone, parts by weight | 0 | 12.5 |
| Part B | | |
| Propylene glycol, parts by weight | 67.0 | 67.0 |
| Sodium Chloride, parts by weight. | 0.5 | 0.5 |

The materials of examples 22 and 23 were mixed together as follows:
1) the ingredients of part A were mixed together; and
2) part B was slowly added to part A using moderate shear mixing.

The materials as prepared were measured for viscosity using a Brookfield viscometer at 25° C. and tested for stability at room temperature, 40° C., and under freeze thaw conditions. Examples 22 and 23 as prepared are cloudy or translucent, indicating they are both emulsions. This is indicative that the propylene glycol and silicone have formed an emulsion consisting of a continuous and a discontinuous phases and both phases are non-aqueous. Table 9 shows the viscosities and stabilities.

TABLE 9

Comparison of Non-Aqueous Emulsion Cosmetic Base with and without Elastomer Gel Swollen by Silicone Oil

| Property | Example 22 | Example 23 |
|---|---|---|
| Elastomer Gel swollen with silicone oil; present? | No | Yes |
| Viscosity, initial, cps at 25° C. | 4,400 | 17,200 |
| Stability, room temperature, 11 days | separated into two layers | homogeneous emulsion, unchanged |
| Stability at 40° C., 9 days | separated into two layers | homogeneous emulsion, unchanged |
| Viscosity after 5 freeze thaw cycles, cps at 25° C. | 3,700 | 16,500 |
| Percent change in viscosity after 5 freeze thaw cycles. | −18.9 | −4.24 |

The incorporation of the silicone oil swollen silicone elastomer enables the preparation of stable salt-comprising (e.g. NaCl) non-aqueous emulsions of other silicones with non-aqueous organic hydroxylic solvents and serves to provide a basic composition useful as a base for a variety of cosmetic and personal care compositions as well as providing a component for topical drug delivery systems. The stability is improved by preservation of the emulsion over five freeze thaw cycles in contrast to the preparation where the elastomer was absent. The stability is improved by preservation of the emulsion against separation into distinct liquid phases for a period of at least eleven days at room temperature, and a period of at least nine days at 40° C. Stability is herein defined as no visible phase separation of the immiscible phases after a given period of time at a given temperature, i.e. a matter of days at a given temperature.

Having described the invention, that which is claimed is:

1. A non-aqueous silicone emulsion, comprising:
   a silicone phase, comprising a crosslinked silicone elastomer and a low molecular weight silicone fluid; and an organic phase, comprising an organic liquid wherein the organic phase comprises less than 50 parts by weight water per 100 parts by weight of the organic phase.

2. The emulsion of claim 1, wherein the silicone phase is a continuous phase, the organic phase is a discontinuous phase and the discontinuous organic phase is dispersed in the continuous silicone phase.

3. The emulsion of claim 1, wherein the emulsion comprises from 0.1 parts by weight to 99.9 parts by weight of the silicone phase and from 0.1 parts by weight to 99.9 parts by weight of the organic phase.

4. The emulsion of claim 1, wherein the silicone phase comprises from 0.005 parts by weight to 30 parts by weight of the crosslinked silicone elastomer and from 70 parts by weight to 99.995 parts by weight of the low molecular weight silicone.

5. The emulsion of claim 1, wherein the crosslinked silicone elastomer is the reaction product of a hydrosilylation reaction between an alkenyl silicone precursor and a hydrogen silicone precursor.

6. The emulsion of claim 5, wherein the alkenyl silicone precursor is organosiloxane or organopolysiloxane having two or more alkenyl groups per molecule on average.

7. The emulsion of claim 6, wherein the alkenyl silicone precursor is an a linear alkenyl stopped polyorganosiloxane having the formula:

$$M^{vi}_a D_x D^{vi}_y M_{2-a}$$

where the subscript x is a number greater than 500, the subscript y is a number ranging from zero to about 20, the subscript a is a number ranging from 0 to 2, subject to the limitation that a+y is within the range of from 1 to about 20, with $M^{vi}$ defined as:

$$R^1 R^2 R^3 SiO_{1/2}$$

where $R^1$ is a monovalent unsaturated hydrocarbon radical having from two to ten carbon atoms, and $R^2$ and $R^3$ are each independently one to forty carbon atom monovalent hydrocarbon radicals, with D defined as:

$$R^4 R^5 SiO_{2/2}$$

where $R^4$ and $R^5$ are each independently one to forty carbon atom monovalent hydrocarbon radicals, with $D^{vi}$ defined as:

$$D^{vi} = R^6 R^7 SiO_{2/2}$$

where $R^6$ is a monovalent unsaturated hydrocarbon radical having from two to ten carbon atoms, and $R^7$ is independently a one to forty carbon atom monovalent hydrocarbon radical with M defined as:

$$M = R^8 R^9 R^{10} SiO_{1/2}$$

with $R^8$, $R^9$, and $R^{10}$ each independently a one to forty carbon atom monovalent hydrocarbon radical.

8. The emulsion of claim 5 wherein the hydrogen silicone precursor is an organohydrogensiloxane having two or more silicon hydride groups per molecule on average.

9. The emulsion of claim 8 wherein the hydrogen silicone precursor is a resin having the formula:

$$(M^H_w Q_z)_j$$

where Q has the formula $SiO_{4/2}$ and where $M^H$ has the formula $H_b R^{11}_{3-b} SiO_{1/2}$ with the subscript b ranging from 1 to 3, where $R^{11}$ is a one to forty carbon atom monovalent hydrocarbon radical; with the subscripts w and z having a ratio of 0.5 to 4.0 respectively, and the subscript j ranging from about 2.0 to about 100.

10. The emulsion of claim 1, wherein the low molecular weight silicone comprises has a viscosity below about 1,000 centistokes at 25° C.

11. The emulsion of claim 10 wherein the low molecular weight silicone is selected from the group consisting of $D_3$, $D_4$, $D_5$, $D_6$ and $M'D'_iM'$ and mixtures thereof where D is defined as:

$$R^4 R^5 SiO_{2/2}$$

where $R^4$ and $R^5$ are each independently one to forty carbon atom monovalent hydrocarbon radicals and D' is independently defined as:

$$R^4 R^5 SiO_{2/2}$$

where $R^4$ and $R^5$ are each independently one to forty carbon atom monovalent hydrocarbon radicals and M' independently has the formula

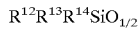

where $R^{12}$, $R^{13}$ and $R^{14}$ are each independently selected from the group of one to forty carbon atom monovalent hydrocarbon radicals and the subscript i ranges from 0 to about 300.

12. The emulsion of claim 11, wherein low molecular weight silicone is selected from the group consisting of $D_3$, $D_4$, $D_5$, $D_6$ and mixtures thereof.

13. The emulsion of claim 1, wherein the organic liquid is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

14. The emulsion of claim 13 wherein said non-aqueous organic hydroxylic solvent is propylene glycol.

15. The emulsion of claim 5, wherein the hydrosilylation reaction is carried out in the presence of a first portion of the low molecular weight silicone to thereby form a gel.

16. The emulsion of claim 15, wherein the gel is slurried in a second portion of the low molecular weight silicone and the slurry so formed is then subjected to further mixing to form a mixture.

17. A personal care composition comprising the emulsion of claim 1.

18. The personal care composition of claim 17, wherein the composition is selected from deodorants, antiperspirants, facial creams, shampoos, mousses, styling gels, sunscreens, lipsticks, foundations, blushes, makeups, and mascaras.

19. A personal care composition, comprising the non-aqueous emulsion of claim 1 and one or more water-sensitive dermatological active agents or cosmetic active agents.

20. A deodorant composition, comprising the non-aqueous emulsion of claim 1 and one or more anti-microbial agents.

21. An antiperspirant composition, comprising the non-aqueous emulsion of claim 1 and one or more active antiperspirant agents.

22. A skin cream composition, comprising the non-aqueous emulsion of claim 1 and an emollient.

23. A sunscreen composition comprising the non-aqueous emulsion of claim 1 and one or more agents for absorbing ultraviolet radiation.

24. A method for making a nonaqueous silicone emulsion, comprising adding a silicone elastomer and a first portion of a low molecular weight silicone together, thereby forming a silicone gel, slurrying the gel with a second portion of the low molecular weight silicone to form a mixture having a desired particle size, thereby forming a silicone phase, and combining the silicone phase with an organic solvent to form the emulsion.

25. The method of claim 24, wherein the silicone phase is a continuous phase, the organic phase is a discontinuous phase and the discontinuous organic phase is dispersed in the continuous phase.

26. The emulsion of claim 1, wherein the organic liquid is a polar liquid that exhibits a dipole moment of from 0.9 to 4.5.

27. The emulsion of claim 1, wherein the organic liquid is a hydroxylic liquid.

28. The emulsion of claim 1, wherein the organic phase comprises less than 30 parts by weight water per 100 parts by weight of the organic phase.

29. The emulsion of claim 1, wherein the organic phase comprises less than 10 parts by weight water per 100 parts by weight of the organic phase.

30. The emulsion of claim 1, wherein the organic phase comprises less than 1 parts by weight water per 100 parts by weight of the organic phase.

* * * * *